US012667364B2

(12) United States Patent
Peelukhana et al.

(10) Patent No.: US 12,667,364 B2
(45) Date of Patent: Jun. 30, 2026

(54) LEFT ATRIAL APPENDAGE CLOSURE DEVICE WITH PASSIVE FIXATION

(71) Applicant: BOSTON SCIENTIFIC SCIMED, INC., Maple Grove, MN (US)

(72) Inventors: Srikara Viswanath Peelukhana, Maple Grove, MN (US); Mark Christian McPhail, Maple Grove, MN (US); Brian Joseph Tischler, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 343 days.

(21) Appl. No.: 18/113,442

(22) Filed: Feb. 23, 2023

(65) Prior Publication Data

US 2023/0270442 A1 Aug. 31, 2023

Related U.S. Application Data

(60) Provisional application No. 63/313,972, filed on Feb. 25, 2022.

(51) Int. Cl.
*A61B 17/12* (2006.01)
*A61B 17/00* (2006.01)
(52) U.S. Cl.
CPC .. *A61B 17/12122* (2013.01); *A61B 17/12172* (2013.01); *A61B 17/12177* (2013.01);
(Continued)
(58) Field of Classification Search
CPC ........ A61B 17/12122; A61B 17/12172; A61B 17/12177; A61B 2017/1205; A61B 2017/00619; A61B 2017/12054
See application file for complete search history.

(56) References Cited

U.S. PATENT DOCUMENTS

| 178,283 A | 6/1876 | French |
| 1,967,318 A | 7/1934 | Monahan |

(Continued)

FOREIGN PATENT DOCUMENTS

| CN | 1399571 A | 2/2003 |
| CN | 202143640 U | 2/2012 |

(Continued)

OTHER PUBLICATIONS

International Search Report and Written Opinion dated May 12, 2023 for International Application No. PCT/US2023/013715.

(Continued)

*Primary Examiner* — Darwin P Erezo
*Assistant Examiner* — Raihan R Khandker
(74) *Attorney, Agent, or Firm* — Seager, Tufte & Wickhem LLP

(57) ABSTRACT

An occlusive medical implant for implantation within a left atrial appendage may include an expandable framework configured to self-expand from a collapsed configuration to an expanded configuration, and an occlusive element disposed on a proximal portion of the expandable framework. At least a portion of the expandable framework may be mechanically expandable from the expanded configuration to a securement configuration. When the occlusive medical implant is disposed within the left atrial appendage, the expandable framework exerts a first radial force on the left atrial appendage in the expanded configuration and the expandable framework exerts a second radial force on the left atrial appendage in the securement configuration. The second radial force is greater than the first radial force.

10 Claims, 18 Drawing Sheets

(52) U.S. Cl.
CPC .............. *A61B 2017/00632* (2013.01); *A61B*
*2017/1205* (2013.01)

(56) References Cited

U.S. PATENT DOCUMENTS

| | | | |
|---|---|---|---|
| 3,402,710 A | 9/1968 | Paleschuck |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,175,545 A | 11/1979 | Termanini |
| 4,309,776 A | 1/1982 | Berguer |
| 4,341,218 A | 7/1982 | Ü |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |

(56) References Cited

U.S. PATENT DOCUMENTS

| | | |
|---|---|---|
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,902,289 A | 5/1999 | Swartz et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muij Van de Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,931,818 A | 8/1999 | Werp et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,954,767 A | 9/1999 | Pajotin et al. |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | Mckenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,159,195 A | 12/2000 | Ha et al. |
| 6,161,543 A | 12/2000 | Cox et al. |
| 6,168,615 B1 | 1/2001 | Ken et al. |
| 6,171,329 B1 | 1/2001 | Shaw et al. |
| 6,179,859 B1 | 1/2001 | Bates et al. |
| 6,193,739 B1 | 2/2001 | Chevillon et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,235,045 B1 | 5/2001 | Barbut et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,772 B1 | 7/2001 | Mulhauser et al. |
| 6,267,776 B1 | 7/2001 | O'Connell |
| 6,270,490 B1 | 8/2001 | Hahnen |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,319,251 B1 | 11/2001 | Tu et al. |
| 6,328,727 B1 | 12/2001 | Frazier et al. |
| 6,328,755 B1 | 12/2001 | Marshall |
| 6,342,062 B1 | 1/2002 | Suon et al. |
| 6,346,116 B1 | 2/2002 | Brooks et al. |
| 6,346,895 B1 | 2/2002 | Lee et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,771 B1 | 6/2002 | Palmer et al. |
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,454,775 B1 | 9/2002 | Demarais et al. |
| 6,458,145 B1 | 10/2002 | Ravenscroft et al. |
| 6,464,712 B1 | 10/2002 | Epstein et al. |
| 6,468,291 B2 | 10/2002 | Bates et al. |
| 6,468,301 B1 | 10/2002 | Amplatz et al. |
| 6,485,501 B1 | 11/2002 | Green |

(56) References Cited

U.S. PATENT DOCUMENTS

| | | |
|---|---|---|
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,533,782 B2 | 3/2003 | Howell et al. |
| 6,547,760 B1 | 4/2003 | Samson et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,569,184 B2 | 5/2003 | Huter |
| 6,569,214 B2 | 5/2003 | Williams et al. |
| 6,589,214 B2 | 7/2003 | McGuckin et al. |
| 6,589,251 B2 | 7/2003 | Yee et al. |
| 6,599,308 B2 | 7/2003 | Amplatz |
| 6,602,271 B2 | 8/2003 | Adams et al. |
| 6,623,508 B2 | 9/2003 | Shaw et al. |
| 6,641,564 B1 | 11/2003 | Kraus |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,712,836 B1 | 3/2004 | Berg et al. |
| 6,726,701 B2 | 4/2004 | Gilson et al. |
| 6,730,108 B2 | 5/2004 | Van Tassel et al. |
| 6,755,812 B2 | 6/2004 | Peterson et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,942,653 B2 | 9/2005 | Quinn |
| 6,949,113 B2 | 9/2005 | Van Tassel et al. |
| 6,958,061 B2 | 10/2005 | Truckai et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,179,275 B2 | 2/2007 | McGuckin, Jr. et al. |
| 7,226,466 B2 | 6/2007 | Opolski |
| 7,303,526 B2 | 12/2007 | Sharkey et al. |
| 7,323,002 B2 | 1/2008 | Johnson et al. |
| 7,597,704 B2 | 10/2009 | Frazier et al. |
| 7,678,123 B2 | 3/2010 | Chanduszko |
| 7,695,425 B2 | 4/2010 | Schweich et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,780,694 B2 | 8/2010 | Palmer et al. |
| 7,799,049 B2 | 9/2010 | Ostrovsky et al. |
| 7,811,300 B2 | 10/2010 | Feller, III et al. |
| 7,811,314 B2 | 10/2010 | Fierens et al. |
| 7,862,500 B2 | 1/2011 | Khairkhahan et al. |
| 7,927,365 B2 | 4/2011 | Fierens et al. |
| 7,972,359 B2 | 7/2011 | Kreidler |
| 8,025,495 B2 | 9/2011 | Hardert et al. |
| 8,043,329 B2 | 10/2011 | Khairkhahan et al. |
| 8,052,715 B2 | 11/2011 | Quinn et al. |
| 8,062,282 B2 | 11/2011 | Kolb |
| 8,080,032 B2 | 12/2011 | van Der Burg et al. |
| 8,097,015 B2 | 1/2012 | Devellian |
| 8,221,384 B2 | 7/2012 | Frazier et al. |
| 8,221,445 B2 | 7/2012 | van Tassel et al. |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,491,623 B2 | 7/2013 | Vogel et al. |
| 8,523,897 B2 | 9/2013 | van Der Burg et al. |
| 8,535,343 B2 | 9/2013 | van Der Burg et al. |
| 8,562,509 B2 | 10/2013 | Bates |
| 8,663,273 B2 | 3/2014 | Khairkhahan et al. |
| 8,685,055 B2 | 4/2014 | VanTassel et al. |
| 8,834,519 B2 | 9/2014 | van Der Burg et al. |
| 8,845,711 B2 | 9/2014 | Miles et al. |
| 9,034,006 B2 | 5/2015 | Quinn et al. |
| 9,132,000 B2 | 9/2015 | VanTassel et al. |
| 9,168,043 B2 | 10/2015 | van Der Burg et al. |
| 9,211,124 B2 | 12/2015 | Campbell et al. |
| 9,445,895 B2 | 9/2016 | Kreidler |
| 9,554,806 B2 | 1/2017 | Larsen et al. |
| 9,561,037 B2 | 2/2017 | Fogarty et al. |
| 9,561,097 B1 | 2/2017 | Kim et al. |
| 9,629,636 B2 | 4/2017 | Fogarty et al. |
| 9,730,701 B2 | 8/2017 | Tischler et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,071,181 B1 | 9/2018 | Penegor et al. |
| 10,076,335 B2 | 9/2018 | Zaver et al. |
| 10,143,458 B2 | 12/2018 | Kreidler |
| 10,575,851 B2 | 3/2020 | Rogers et al. |
| 10,952,736 B2 | 3/2021 | Krishnan |
| 2001/0000797 A1 | 5/2001 | Mazzocchi |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082638 A1 | 6/2002 | Porter et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0017775 A1 | 1/2003 | Dong et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0204203 A1 | 10/2003 | Khairkhahan et al. |
| 2003/0208214 A1 | 11/2003 | Loshakove et al. |
| 2003/0220667 A1 | 11/2003 | van der Burg et al. |
| 2004/0034366 A1 | 2/2004 | van der Burg et al. |
| 2004/0049210 A1 | 3/2004 | VanTassel et al. |
| 2004/0093012 A1 | 5/2004 | Cully et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0158274 A1 | 8/2004 | WasDyke |
| 2004/0186486 A1 | 9/2004 | Roue et al. |
| 2004/0215230 A1 | 10/2004 | Frazier et al. |
| 2004/0220610 A1 | 11/2004 | Kreidler et al. |
| 2004/0220682 A1 | 11/2004 | Levine et al. |
| 2004/0230222 A1 | 11/2004 | van der Burg et al. |
| 2005/0004652 A1 | 1/2005 | van der Burg et al. |
| 2005/0015109 A1 | 1/2005 | Lichtenstein |
| 2005/0038470 A1 | 2/2005 | van der Burg et al. |
| 2005/0049573 A1 | 3/2005 | Van Tassel et al. |
| 2005/0070952 A1 | 3/2005 | Devellian |
| 2005/0113861 A1 | 5/2005 | Corcoran et al. |
| 2005/0125020 A1 | 6/2005 | Meade et al. |

(56)  References Cited

U.S. PATENT DOCUMENTS

| | | |
|---|---|---|
| 2005/0177182 A1* | 8/2005 | van der Burg ... A61B 17/12022 |
| | | 606/157 |
| 2005/0203568 A1 | 9/2005 | Burg et al. |
| 2005/0273129 A1 | 12/2005 | Michels et al. |
| 2005/0283186 A1 | 12/2005 | Berrada et al. |
| 2005/0288704 A1 | 12/2005 | Cartier et al. |
| 2006/0015136 A1 | 1/2006 | Besselink |
| 2006/0030877 A1 | 2/2006 | Martinez et al. |
| 2006/0052816 A1 | 3/2006 | Bates et al. |
| 2006/0100658 A1 | 5/2006 | Obana et al. |
| 2006/0155323 A1 | 7/2006 | Porter et al. |
| 2007/0066993 A1 | 3/2007 | Kreidler |
| 2007/0083227 A1 | 4/2007 | van der Burg et al. |
| 2007/0083230 A1 | 4/2007 | Javois |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0324585 A1 | 12/2010 | Miles et al. |
| 2011/0054515 A1 | 3/2011 | Bridgeman et al. |
| 2011/0082495 A1 | 4/2011 | Ruiz |
| 2011/0098525 A1 | 4/2011 | Kermode et al. |
| 2011/0218566 A1 | 9/2011 | van Der Burg et al. |
| 2011/0301630 A1 | 12/2011 | Hendriksen et al. |
| 2012/0029553 A1 | 2/2012 | Quinn et al. |
| 2012/0035643 A1 | 2/2012 | Khairkhahan et al. |
| 2012/0065662 A1 | 3/2012 | van Der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0283585 A1 | 11/2012 | Werneth et al. |
| 2012/0283773 A1 | 11/2012 | Van Tassel et al. |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0110154 A1 | 5/2013 | van Der Burg et al. |
| 2013/0165735 A1 | 6/2013 | Khairkhahan et al. |
| 2013/0166017 A1 | 6/2013 | Cartledge et al. |
| 2013/0211492 A1 | 8/2013 | Schneider et al. |
| 2013/0331884 A1 | 12/2013 | Van Der Burg et al. |
| 2014/0018841 A1 | 1/2014 | Peiffer et al. |
| 2014/0039536 A1 | 2/2014 | Cully et al. |
| 2014/0046360 A1 | 2/2014 | van Der Burg et al. |
| 2014/0081314 A1 | 3/2014 | Zaver et al. |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0303719 A1 | 10/2014 | Cox et al. |
| 2014/0336612 A1 | 11/2014 | Frydlewski et al. |
| 2014/0336699 A1 | 11/2014 | van Der Burg et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van Der Burg et al. |
| 2016/0192942 A1 | 7/2016 | Strauss et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0100112 A1 | 4/2017 | van Der Burg et al. |
| 2017/0181751 A1 | 6/2017 | Larsen et al. |
| 2017/0340336 A1 | 11/2017 | Osypka |
| 2018/0064446 A1 | 3/2018 | Figulla et al. |
| 2018/0070950 A1 | 3/2018 | Zaver et al. |
| 2018/0085130 A1 | 3/2018 | Fung et al. |
| 2018/0140412 A1 | 5/2018 | Sutton et al. |
| 2018/0140413 A1 | 5/2018 | Quinn et al. |
| 2018/0250014 A1 | 9/2018 | Melanson et al. |
| 2019/0223883 A1 | 7/2019 | Anderson et al. |
| 2019/0247053 A1 | 8/2019 | Inouye |
| 2019/0298382 A1 | 10/2019 | Fung et al. |
| 2019/0321020 A1 | 10/2019 | Sternik |
| 2020/0229837 A1 | 7/2020 | Ibrahim et al. |
| 2022/0370079 A1* | 11/2022 | Harari .............. A61B 17/12172 |
| 2023/0263528 A1* | 8/2023 | Jones ............... A61B 17/12172 |
| | | 606/1 |

FOREIGN PATENT DOCUMENTS

| | | |
|---|---|---|
| CN | 106859722 A | 6/2017 |
| DE | 10201004476 A1 | 3/2012 |
| EP | 1523957 A2 | 4/2005 |
| EP | 1595504 A1 | 11/2005 |
| EP | 2074953 A1 | 1/2009 |
| EP | 2481381 A1 | 8/2012 |
| EP | 2928420 A1 | 10/2015 |
| EP | 3072461 A1 | 9/2016 |
| EP | 3372173 A2 | 9/2018 |
| JP | 2003532457 A | 11/2003 |
| JP | 2005324019 A | 11/2005 |
| JP | 2007513684 A | 5/2007 |
| JP | 2009160402 A | 7/2009 |
| JP | 2012501793 A | 1/2012 |
| WO | 9313712 A1 | 7/1993 |
| WO | 9504132 A1 | 2/1995 |
| WO | 9522359 A1 | 8/1995 |
| WO | 9601591 A1 | 1/1996 |
| WO | 9640356 A1 | 12/1996 |
| WO | 9721402 A1 | 6/1997 |
| WO | 9726939 A1 | 7/1997 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9822026 A1 | 5/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 9959479 A1 | 11/1999 |
| WO | 0001308 A1 | 1/2000 |
| WO | 0016705 A1 | 3/2000 |
| WO | 0027292 A1 | 5/2000 |
| WO | 0035352 A1 | 6/2000 |
| WO | 0053120 A1 | 9/2000 |
| WO | 0067669 A1 | 11/2000 |
| WO | 0108743 A1 | 2/2001 |
| WO | 0115629 A1 | 3/2001 |
| WO | 0121247 A1 | 3/2001 |

(56) References Cited

FOREIGN PATENT DOCUMENTS

| WO | 0126726 | A1 | 4/2001 |
|---|---|---|---|
| WO | 0130266 | A1 | 5/2001 |
| WO | 0130267 | A1 | 5/2001 |
| WO | 0130268 | A1 | 5/2001 |
| WO | 0170119 | A1 | 9/2001 |
| WO | 0215793 | A2 | 2/2002 |
| WO | 0224106 | A2 | 3/2002 |
| WO | 02071977 | A2 | 9/2002 |
| WO | 03007825 | A1 | 1/2003 |
| WO | 03008030 | A2 | 1/2003 |
| WO | 03032818 | A1 | 4/2003 |
| WO | 2004012629 | A1 | 2/2004 |
| WO | 2007044536 | A1 | 4/2007 |
| WO | 2010024801 | A1 | 3/2010 |
| WO | 2010081033 | A1 | 7/2010 |
| WO | 2013060855 | A1 | 5/2013 |
| WO | 2013159065 | A1 | 10/2013 |
| WO | 2014011865 | A1 | 1/2014 |
| WO | 2014018907 | A1 | 1/2014 |
| WO | 2014089129 | A1 | 6/2014 |
| WO | 201406239 | A1 | 7/2014 |
| WO | 2015164836 | A1 | 10/2015 |
| WO | 2016087145 | A1 | 6/2016 |
| WO | 2018017935 | A1 | 1/2018 |
| WO | 2018187732 | A1 | 10/2018 |
| WO | 2019084358 | A1 | 5/2019 |

OTHER PUBLICATIONS

International Search Report and Written Opinion dated Aug. 3, 2004 for International Application No. PCT/US2004/008109.

International Search Report and Written Opinion dated Feb. 15, 2000 for International Application No. PCT/US99/26325.

International Search Report dated May 20, 2003 for International Application No. PCT/US02/33808.

Written Opinion dated Nov. 17, 2003 for International Application No. PCT/US/02/33808.

International Search Report and Written Opinion dated Aug. 21, 2018 for International Application No. PCT/US2018/029684.

Cragg et al., "A New Percutaneous Vena Cava Filter," American Journal of Radiology, Sep. 1983, pp. 601-604, vol. 141.

Cragg et al., "Nonsurgical Placement of Arterial Endoprostheses: A New Technique Using Nitinol Wire," Radiology, Apr. 1983, pp. 261-263, vol. 147, No. 1.

Lock et al., "Transcatheter Closure of Atrial Septal Defects." Circulation, May 1989, pp. 1091-1099, vol. 79, No. 5.

Lock et al., "Transcatheter Umbrella Closure of Congenital Heart Defects," Circulation, Mar. 1987, pp. 593-599, vol. 75, No. 3.

Rashkind et al., "Nonsurgical closure of patent ductus arteriosus: clinical application of the Rashkind PDA Occluder System," Circulation, Mar. 1987, pp. 583-592, vol. 75, No. 3.

Rosengart et al., "Percutaneous and Minimally Invasive Valve Procedures," Circulation, Apr. 1, 2008, pp. 1750-1767, vol. 117.

Ruttenberg, "Nonsurgical Therapy of Cardiac Disorders," Pediatric Consult, 1986, Pages not numbered, vol. 5, No. 2.

Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.

Wessel et al., "Outpatient Closure of the Patent Ductus Arteriousus," Circulation, 1988, pp. 1068-1071, vol. 77, No. 5.

Tung et al., U.S. Appl. No. 61/559,941, filed Nov. 15, 2011.

Yue Yu et al., U.S. Appl. No. 61/557,880, filed Dec. 20, 2011.

Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.

International Search Report and Written Opinion dated Apr. 22, 2014 for International Application No. PCT/US2013/078454.

Aryana et al., "Incomplete Closure of the Left Atrial Appendage: Implication and Management." Curr Cardiol Rep., 18(9):82, 2016.

Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.

University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.

Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.

Romero et al., "Left Atrial Appendage Closure Devices," Clinical Medicine Insights: Cardiology, vol. 8, pp. 45-52, 2014.

Invitation to Pay Additional Fees and, Where Applicable, Protest Fee, mailed Oct. 13, 2016.

International Search Report and Written Opinion dated Oct. 14, 2019 for International Application No. PCT/US2019/047452.

International Search Report and Written Opinion dated Oct. 27, 2017 for International Application No. PCT/US2017/048150.

International Search Report and Written Opinion dated Jan. 21, 2019 for International Application No. PCT/US2018/051953.

International Search Report and Written Opinion dated Oct. 13, 2016 for International Application No. PCT/US2016/043363.

International Search Report and Written Opinion dated Mar. 17, 2020, for International Application No. PCT/US2019/065243.

International Search Report and Written Opinion dated Sep. 9, 2019 for International Application No. PCT/US2019/033698.

Blackshear et al; "Appendage Obliteration to Reduce Stroke in Cardiac Surgical Patients with Atrial Fibrillation", Ann. Thoracic Surgery, pp. 755-759, 1996.

Lindsay, "Obliteration of the Left Atrial Appendage: A Concept Worth Testing", Ann. Thoracic Surgery, 1996.

Invitation to Pay Additional Fees dated Feb. 22, 2019 for International Application No. PCT/US2018/066163.

International Search Report and Written Opinion dated Oct. 23, 2020 for International Application No. PCT/US2020/042192.

* cited by examiner

LEFT ATRIAL APPENDAGE CLOSURE DEVICE WITH PASSIVE FIXATION

CROSS-REFERENCE TO RELATED APPLICATIONS

This application claims the benefit of priority of U.S. Provisional Application No. 63/313,972, filed Feb. 25, 2022, the entire disclosure of which is hereby incorporated by reference.

TECHNICAL FIELD

The disclosure relates generally to medical devices and more particularly to medical devices that are adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. There is an ongoing need to provide alternative medical devices as well as alternative methods for manufacturing and using medical devices.

SUMMARY

In one example, an occlusive medical implant for implantation within a left atrial appendage may comprise an expandable framework configured to self-expand from a collapsed configuration to an expanded configuration, and an occlusive element disposed on a proximal portion of the expandable framework. At least a portion of the expandable framework may be mechanically expandable from the expanded configuration to a securement configuration. When the occlusive medical implant is disposed within the left atrial appendage, the expandable framework may exert a first radial force on the left atrial appendage in the expanded configuration and the expandable framework may exert a second radial force on the left atrial appendage in the securement configuration. The second radial force may be greater than the first radial force.

In addition or alternatively to any example described herein, the occlusive medical implant may further comprise a proximal hub fixedly attached to a proximal end of the expandable framework, a distal hub fixedly attached to a distal end of the expandable framework, a proximal beam extending distally from the proximal hub within an interior of the expandable framework, and a distal beam extending proximally from the distal hub within the interior of the expandable framework. The distal beam is engaged with the proximal beam.

In addition or alternatively to any example described herein, the distal beam is axially movable relative to the proximal beam.

In addition or alternatively to any example described herein, the proximal beam is fixedly attached to the proximal hub.

In addition or alternatively to any example described herein, the distal beam is rotatable relative to the distal hub.

In addition or alternatively to any example described herein, the distal beam is rotatable relative to the proximal beam.

In addition or alternatively to any example described herein, rotation of the distal beam changes an axial position of the distal hub relative to the proximal hub.

In addition or alternatively to any example described herein, the distal beam is nonrotatable relative to the proximal beam.

In addition or alternatively to any example described herein, the proximal beam is rotatable relative to the proximal hub.

In addition or alternatively to any example described herein, the distal beam is fixedly attached to the distal hub.

In addition or alternatively to any example described herein, rotation of the proximal beam changes an axial position of the distal hub relative to the proximal hub.

In addition or alternatively to any example described herein, the distal beam is a coil spring.

In addition or alternatively to any example described herein, the occlusive medical implant may further include a plurality of support struts extending radially outward from the distal beam to the expandable framework.

In addition or alternatively to any example described herein, the occlusive medical implant may further include a second occlusive element disposed on a distal portion of the expandable framework. A thickness of the second occlusive element is greater than a thickness of the occlusive element, or a surface roughness of the second occlusive element is greater than a surface roughness of the occlusive element, or a coefficient of friction between the second occlusive element and the left atrial appendage is greater than a coefficient of friction between the occlusive element and the left atrial appendage, or a porosity of the second occlusive element is greater than a porosity of the occlusive element.

In addition or alternatively to any example described herein, a medical device system may comprise a catheter having a lumen extending from a proximal opening to a distal opening, a core wire slidably disposed within the lumen, and an occlusive medical implant for implantation within a left atrial appendage releasably attached at a distal end of the core wire. The occlusive medical implant may comprise an expandable framework configured to self-expand from a collapsed configuration to an expanded configuration when unconstrained by the catheter, and an occlusive element disposed over at least a portion of the expandable framework. At least a portion of the expandable framework may be mechanically expandable from the expanded configuration to a securement configuration. When the occlusive medical implant is disposed within the left atrial appendage, the expandable framework may exert a first radial force on the left atrial appendage in the expanded configuration and the expandable framework may exert a second radial force on the left atrial appendage in the securement configuration. The second radial force may be greater than the first radial force.

In addition or alternatively to any example described herein, the core wire is nonrotatably secured to the occlusive medical implant.

In addition or alternatively to any example described herein, the medical device system may further comprise a locking pin engaged with the occlusive medical implant and the core wire, and a pull wire fixed to the locking pin and extending proximally from the occlusive medical implant. The pull wire may be configured to disengage the locking pin from the occlusive medical implant and the core wire to release the occlusive medical implant from the core wire.

In addition or alternatively to any example described herein, the core wire is rotatable relative to the occlusive medical implant.

In addition or alternatively to any example described herein, the expandable framework is devoid of radially protruding anchor elements.

In addition or alternatively to any example described herein, an occlusive medical implant for implantation within a left atrial appendage may comprise an expandable framework configured to self-expand from a collapsed configuration to an expanded configuration, and an occlusive element disposed on a proximal portion of the expandable framework. At least a portion of the expandable framework may be mechanically expandable from the expanded configuration to a securement configuration. The expandable framework has a first radialmost outer extent in the expanded configuration and a second radialmost outer extent in the securement configuration. The second radialmost outer extent may be greater than the first radialmost outer extent.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings, in which.

Figure 1:
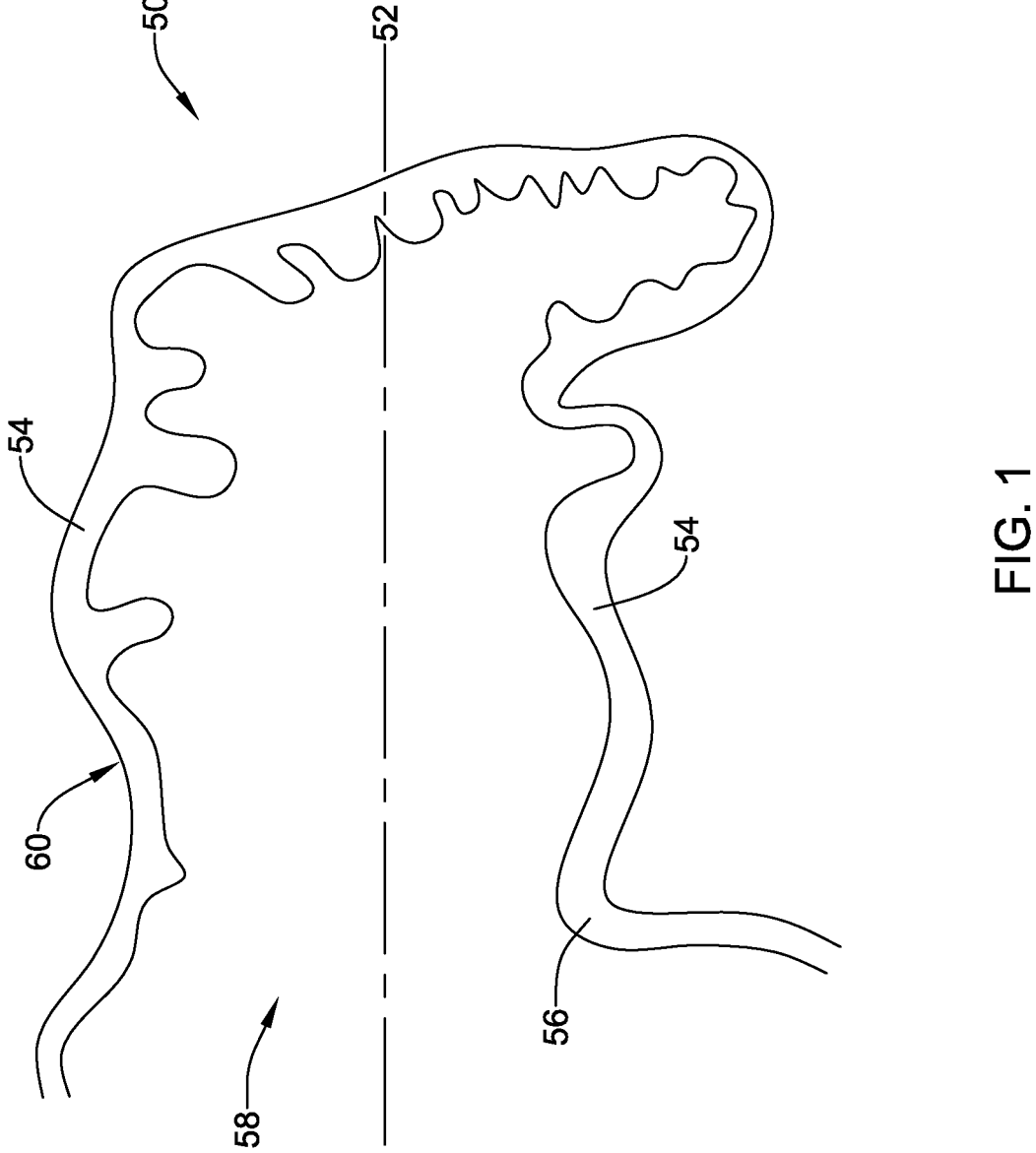
FIG. 1 is a partial cross-sectional view of a left atrial appendage.

While aspects of the disclosure are amenable to various modifications and alternative forms, examples are shown in the drawings and described herein. It should be understood, however, that the intention is not to limit aspects of the disclosure to the particular embodiments described. On the contrary, the disclosure shall cover all modifications, equivalents, and alternatives falling within the spirit and scope thereof.

DETAILED DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the present disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following figures illustrate selected components and/or arrangements of an implant for occluding the left atrial appendage, a system for occluding the left atrial appendage, and/or methods of using the implant and/or the system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the implant and/or the system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

FIG. 1 is a partial cross-sectional view of a left atrial appendage 50. In some examples, the left atrial appendage (LAA) 50 may have a complex geometry and/or irregular surface area. Those skilled in the art will recognize that the illustrated LAA is merely one of many possible shapes and sizes for the LAA, which may vary from patient to patient. Those of skill in the art will also recognize that the medical devices, systems, and/or methods disclosed herein may be adapted for various sizes and shapes of the LAA, as necessary. The left atrial appendage 50 may include a generally longitudinal axis 52 arranged along a depth of a main body 60 of the left atrial appendage 50. The main body 60 may include a lateral wall 54 and an ostium 56 forming a proximal mouth 58. In some examples, a lateral extent of the ostium 56 and/or the lateral wall 54 may be smaller or less than a depth of the main body 60 along the longitudinal axis 52, or a depth of the main body 60 may be greater than a lateral extent of the ostium 56 and/or the lateral wall 54. In some examples, the left atrial appendage 50 may narrow quickly along the depth of the main body 60 or the left atrial appendage may maintain a generally constant lateral extent along a majority of depth of the main body 60. In some examples, the left atrial appendage 50 may include a distalmost region formed or arranged as a tail-like element associated with a distal portion of the main body 60. In some examples, the distalmost region may protrude radially or laterally away from the longitudinal axis 52.

Figure 2:
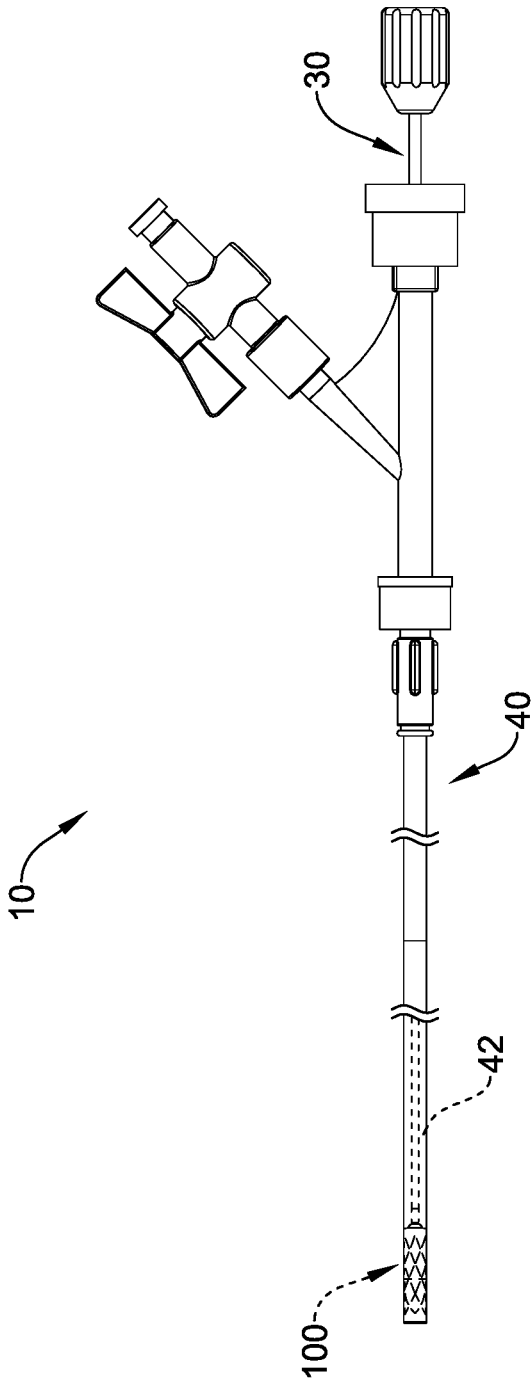
FIGS. 2-3 are side views of an example system for occluding a left atrial appendage.
Figure 3:
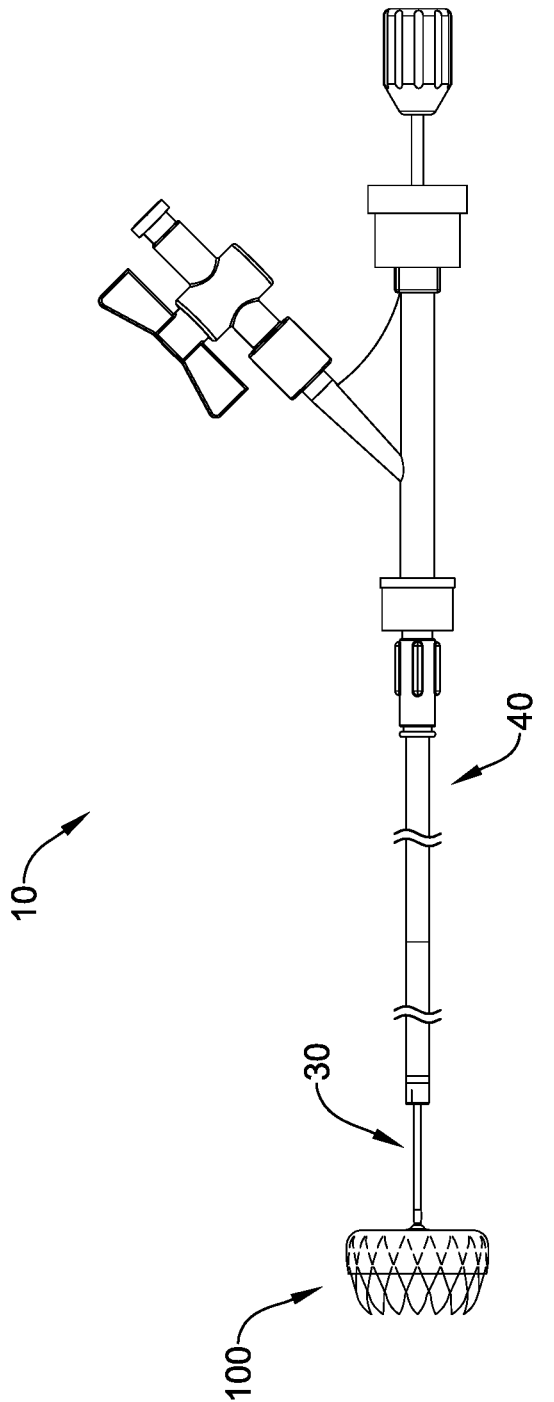

FIGS. 2-3 schematically illustrate selected components and/or arrangements of a medical device system 10. It should be noted that in any given figure, some features of the medical device system 10 may not be shown, or may be shown schematically, for simplicity. Additional details regarding some of the components of the medical device system 10 may be illustrated in other figures in greater detail. The medical device system 10 may be used to deliver and/or deploy a variety of medical implants (e.g., a cardiovascular medical implant, an occlusive medical implant, a replacement heart valve implant, etc.) to one or more locations within the anatomy, including but not limited to, in some embodiments, the heart and/or the LAA. In the interest of clarity, the following discussion refers to an occlusive medical implant, but other medical implants may be used and/or considered with the medical device system 10.

The medical device system 10 may include a catheter 40 having a lumen 42 extending from a proximal opening to a distal opening, a core wire 30 slidably and/or rotatably disposed within the lumen 42, and an occlusive medical implant 100 for implantation within a left atrial appendage releasably attached at and/or to a distal end of the core wire 30. In some embodiments, the core wire 30 may be nonrotatably secured to the occlusive medical implant 100. In some embodiments, the core wire 30 may be rotatable relative to the occlusive medical implant 100. Other configurations are also contemplated. In some embodiments, a proximal end of the core wire 30 may extend proximally of a proximal end of the catheter 40 and/or the proximal opening of the lumen 42 for manual manipulation by a clinician or practitioner. Some suitable, but non-limiting, examples of materials for the medical device system 10, the core wire 30, and/or the catheter 40, etc., including but not limited to metallic materials, polymeric materials, etc., are discussed below. It is contemplated that any and/or all example occlusive medical implants disclosed herein may be used in accordance with and/or be associated with the medical device system 10 described above.

The occlusive medical implant 100 may include an expandable framework 110 (e.g., FIG. 4) configured to self-expand from a collapsed configuration (e.g., FIG. 2), such as when the occlusive medical implant 100 is disposed within the lumen 42 proximate the distal opening, to an expanded configuration (e.g., FIGS. 3-4), when the occlusive medical implant 100 is unconstrained by the catheter 40. In at least some embodiments, at least a portion of the expandable framework 110 may be mechanically expandable from the expanded configuration (e.g., FIGS. 3-4) to a securement configuration, as described herein.

Figure 4:
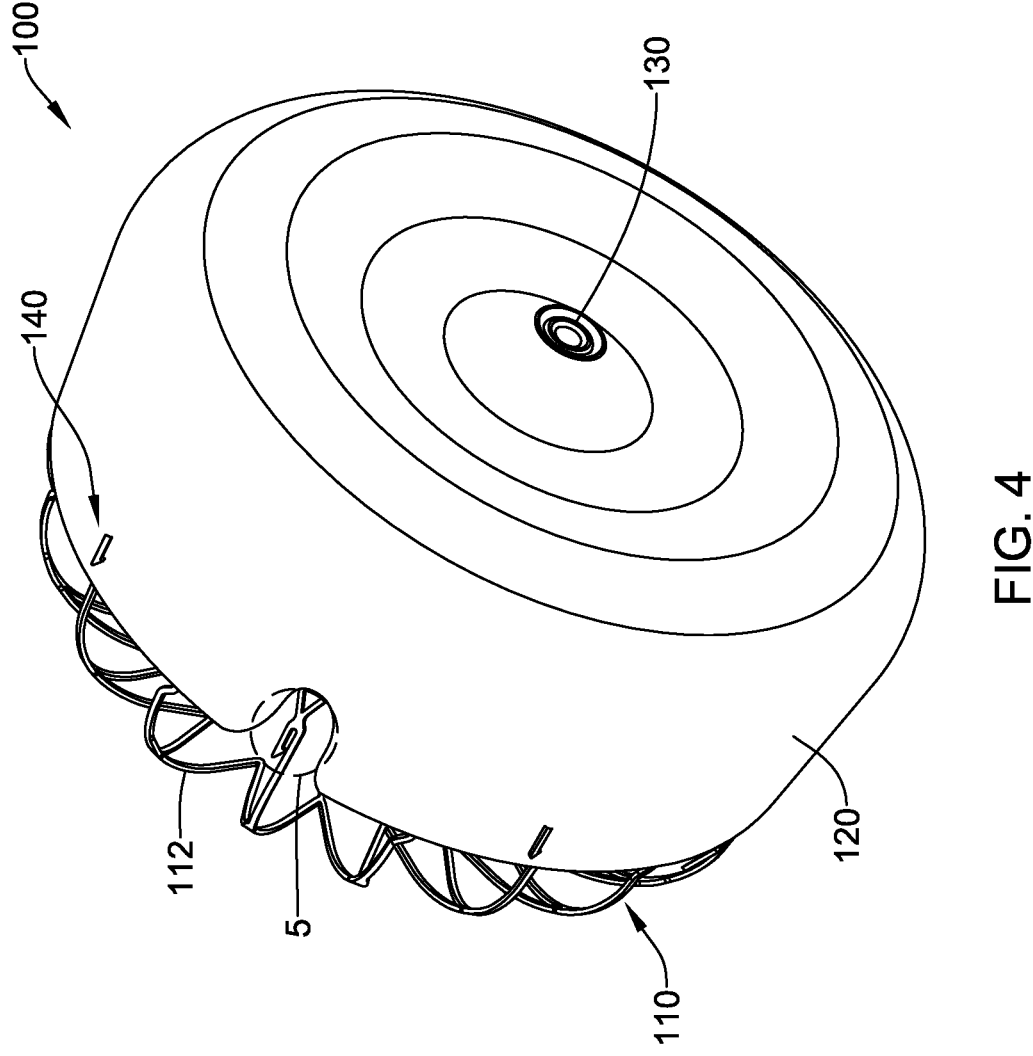
FIGS. 4-5 illustrate selected aspects of an implant for occluding a left atrial appendage.

FIG. 4 illustrates an example configuration of the occlusive medical implant 100 comprising the expandable framework 110 configured to self-expand from the collapsed configuration to the expanded configuration. The expandable framework 110 may comprise a plurality of interconnected struts 112. In some embodiments, the expandable framework 110 may be compliant and substantially conform to and/or be in sealing engagement with the shape and/or geometry of the lateral wall 54 of the left atrial appendage 50 in the expanded configuration. In some embodiments, the occlusive medical implant 100 may expand to a size, extent, or shape less than or different from a maximum unconstrained extent, as determined by the surrounding tissue and/or the lateral wall 54 of the left atrial appendage 50. In at least some embodiments, the expandable framework 110 may be devoid of radially protruding anchor elements (e.g., spikes, barbs, hooks, etc. extending radially outward of and/or from the expandable framework 110) configured to engage with and/or pierce the lateral wall 54 of the left atrial appendage to anchor the occlusive medical implant 100 within the left atrial appendage 50.

In some embodiments, a proximal end of the expandable framework 110 may be configured to releasably attach, join, couple, engage, or otherwise connect to the distal end of the core wire 30 (e.g., FIG. 3). In some embodiments, the proximal end of the expandable framework 110 may include a proximal hub 130 coupled thereto. In some embodiments, the proximal hub 130 may be configured to and/or adapted to releasably couple with, join to, mate with, or otherwise engage a distal end of the core wire 30. Other means of releasably coupling and/or engaging the proximal hub 130 of the expandable framework 110 to the distal end of the core wire 30 are also contemplated.

In some embodiments, the occlusive medical implant 100 may include an occlusive element 120 (e.g., a membrane, a fabric, or a tissue element, etc.) connected to, disposed on, disposed over, disposed about, or covering a proximal portion 114 of the expandable framework 110 and/or the plurality of interconnected struts 112. In some embodiments, the occlusive element 120 may be connected to, disposed on, disposed over, disposed about, or cover a proximal portion of an outer (or outwardly facing) surface of the expandable framework 110 and/or the plurality of interconnected struts 112. In some embodiments, the occlusive element 120 may be connected to, disposed on, disposed over, disposed about, or covering the proximal end of the expandable framework 110.

Figure 5:
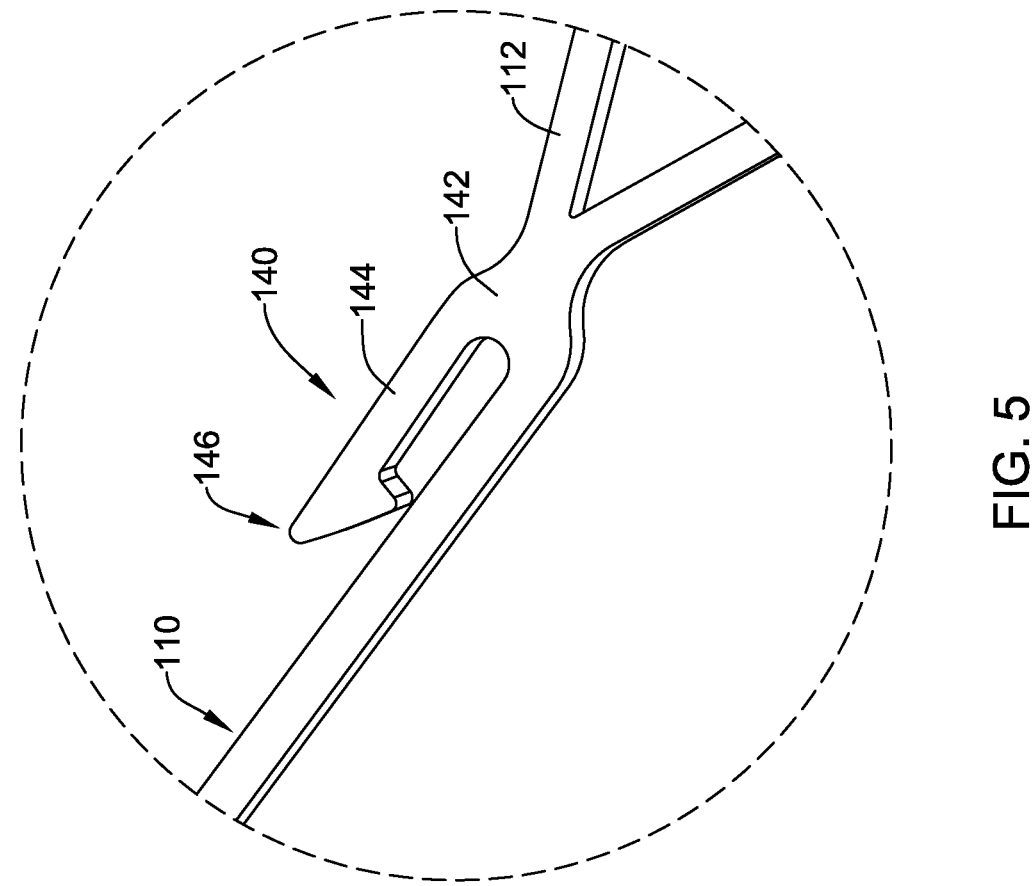

In some embodiments, the occlusive medical implant 100 and/or the expandable framework 110 may include a plurality of securement members 140 connected to the plurality of interconnected struts 112. Each of the plurality of securement members 140 may include a base portion 142 attached to the plurality of interconnected struts 112, a tip portion 146, and a body portion 144 extending from the base portion 142 to the tip portion 146, as seen in FIG. 5 for example. In some embodiments, the tip portion 146 of each of, some of, or one of the plurality of securement members 140 may be radially aligned with the plurality of interconnected struts 112 (e.g., on a common circumference). In some embodiments, the body portion 144 and/or the tip portion 146 of the plurality of securement members 140 may be oriented substantially parallel to the plurality of interconnected struts 112. In some embodiments, the tip portion 146 of each of, some of, or one of the plurality of securement members 140 does not extend radially outward of the plurality of interconnected struts 112. As such, the plurality of securement members 140 and/or the tip portion 146 of the plurality of securement members 140 may be incapable of engaging with, extending into, and/or piercing native tissue(s) disposed outside of (e.g., radially outward of, etc.) the expandable framework 110 and/or the plurality of interconnected struts 112. Some suitable, but non-limiting, examples of materials for the occlusive medical implant 100, the expandable framework 110, the plurality of interconnected struts 112, etc., including but not limited to metallic materials, polymeric materials, etc., are discussed below.

In some embodiments, the tip portion 146 of the plurality of securement members 140 may be capable of piercing the occlusive element 120. In some embodiments, the occlusive element 120 may optionally include one or more holes or apertures configured to receive the tip portion 146 and/or the body portion 144 of each of, some of, or one of the plurality of securement members 140. Each of, some of, or one of the plurality of securement members 140 may extend through the occlusive element 120 at least once (e.g., from the inner surface to the outer surface, from the outer surface to the inner surface), as seen in FIG. 4 for example. In some embodiments, each of, some of, or one of the plurality of securement members 140 may extend through the occlusive element 120 multiple times.

In some embodiments, the occlusive element 120 may be permeable or impermeable to blood and/or other fluids, such as water. In some embodiments, the occlusive element 120 may include a polymeric membrane, a metallic or polymeric mesh, a porous or semi-porous filter-like material, or other suitable construction. In some embodiments, the occlusive element 120 prevents thrombi (e.g., blood clots, etc.) from passing through the occlusive element 120 and out of the left atrial appendage 50 into the blood stream. In some embodiments, the occlusive element 120 promotes endothelization after implantation, thereby effectively removing the target site (e.g., the left atrial appendage 50, etc.) from the patient's circulatory system. Some suitable, but non-limiting, examples of materials for the occlusive element 120 are discussed below.

In some embodiments, the expandable framework 110, the plurality of interconnected struts 112, and/or the plurality of securement members 140 may be integrally formed and/or cut from a unitary member. In some embodiments, the expandable framework 110, the plurality of interconnected struts 112, and/or the plurality of securement members 140 may be integrally formed and/or cut from a unitary tubular member and subsequently formed and/or heat set to a desired shape in the expanded configuration. In some embodiments, the expandable framework 110, the plurality of interconnected struts 112, and/or the plurality of securement members 140 may be integrally formed and/or cut from a unitary flat member or sheet, and then rolled or formed into a tubular structure and subsequently formed and/or heat set to the desired shape in the expanded configuration. Some exemplary means and/or methods of making and/or forming the expandable framework 110 include laser cutting, machining, punching, stamping, electro discharge machining (EDM), chemical dissolution, etc. Other means and/or methods are also contemplated.

FIGS. 6-17 illustrate selected aspects of embodiments according to the disclosure. Any and/or all of the aspects shown in FIGS. 3-4 and discussed herein with respect to the occlusive medical implant 100 and/or the medical device system 10 may be used with and/or applied to any other embodiment of an occlusive medical implant disclosed herein. Similarly, any and/or all of the aspects shown in FIGS. 6-17 and discussed herein may be used with and/or applied to the occlusive medical implant 100 and/or the medical device system 10. In the interest of brevity, common and/or like elements will be referred to using the lxx reference numerals associated with FIGS. 3-4. In the interest of clarity, some elements associated with the medical device system 10 and/or the occlusive medical implant 100 may be omitted from the figures.

As discussed herein, at least a portion of the expandable framework 110 may be mechanically expandable from the expanded configuration to a securement configuration. The various embodiments and/or examples discussed herein may include different mechanisms and/or means for mechanically expanding at least a portion of the expandable framework 110 to the securement configuration. It shall be noted that at any time prior to mechanically expanding at least a portion of the expandable framework 110 to the securement configuration, regardless of configuration and/or embodiment, the expandable framework 110 and/or the occlusive medical implant 100 maybe recaptured within the lumen 42 of the catheter 40, which may include shifting the expandable framework 110 from the expanded configuration to the collapsed configuration, and repositioned. In some embodiments, mechanical expansion of at least a portion of the expandable framework 110 to the securement configuration may be reversible, thereby permitting recapture and repositioning of the occlusive medical implant. In some embodiments, mechanical expansion of at least a portion of the expandable framework 110 to the securement configuration may be irreversible, and thus recapture of the occlusive medical implant may not be possible without permanently and/or irreversibly damaging the occlusive medical implant, rendering it unsuitable for implantation.

Figure 6:
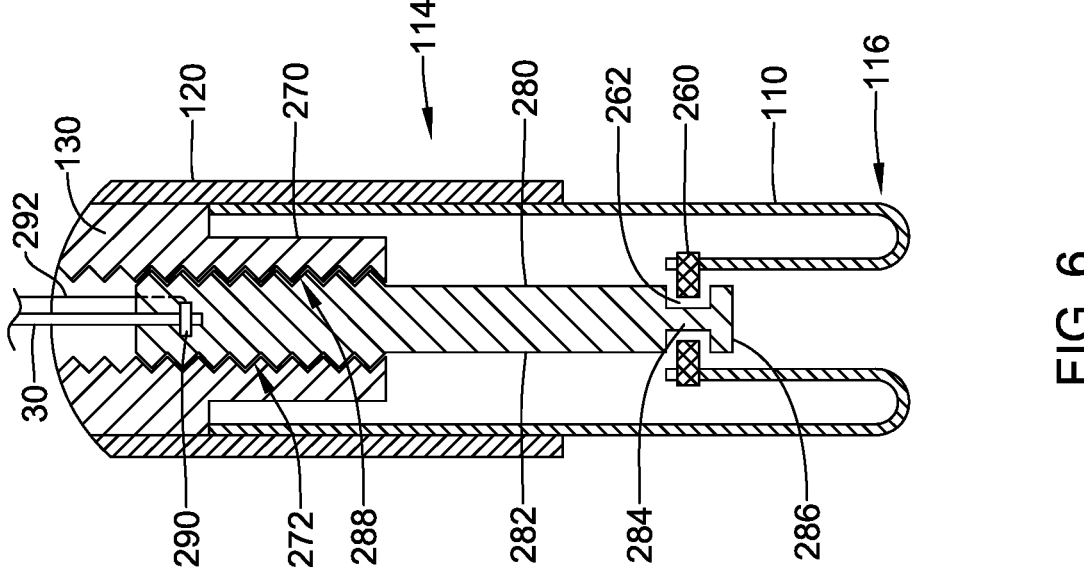
FIGS. 6-8 are partial cross-sectional views illustrating selected aspects of the implant of FIGS. 4-5.
Figure 7:
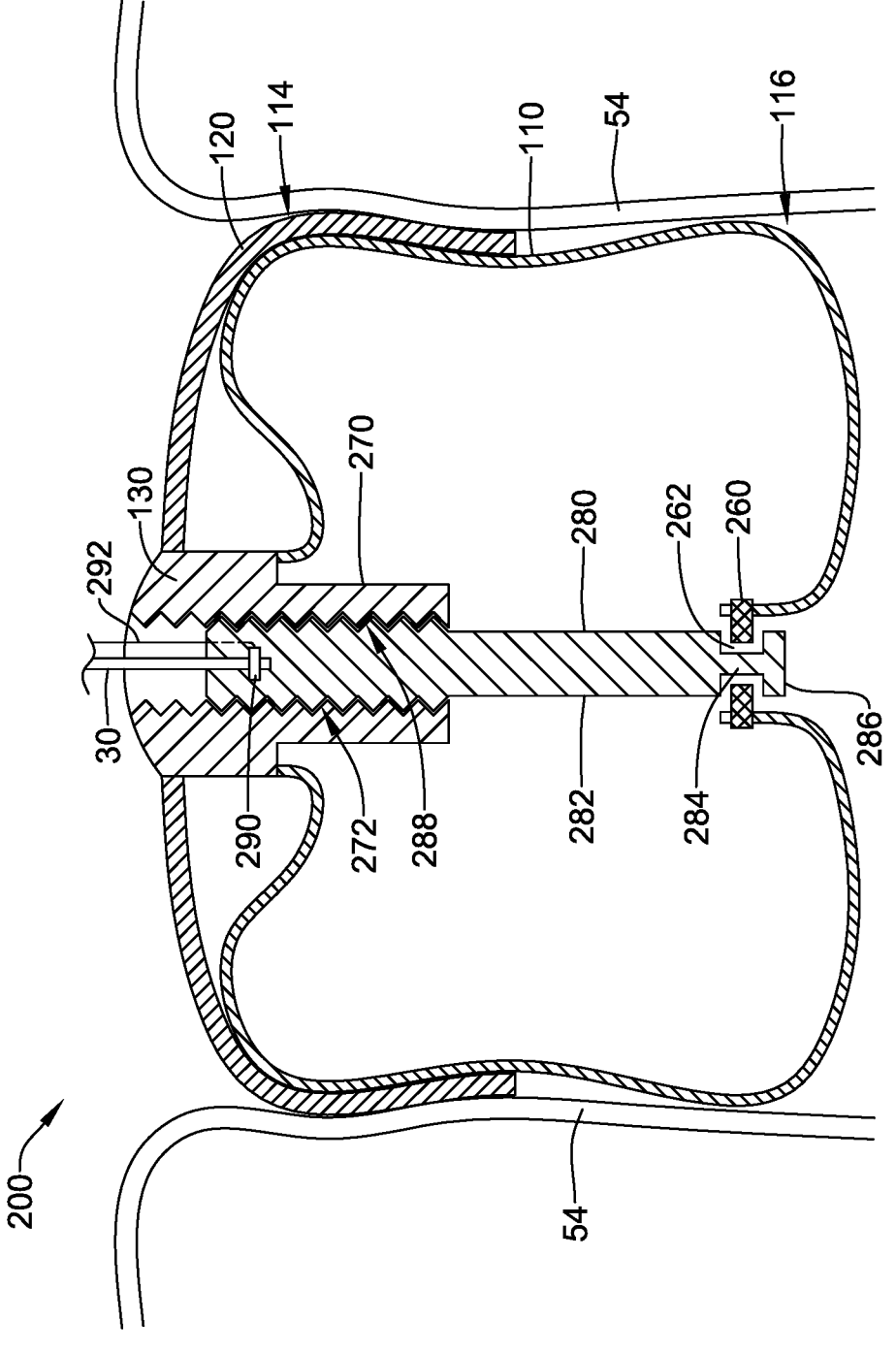
Figure 8:
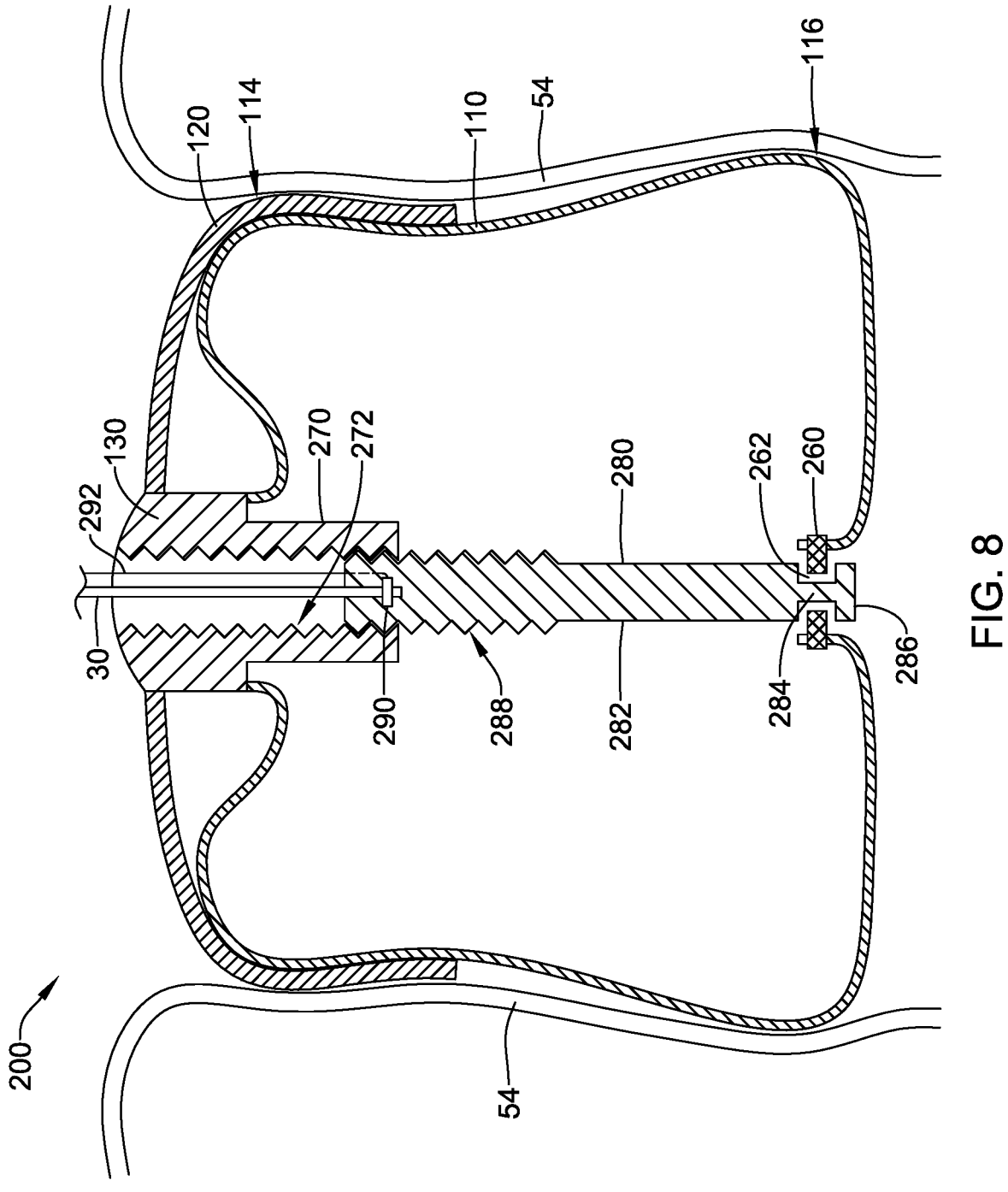

FIGS. 6-8 illustrate selected aspects of one example embodiment of an occlusive medical implant 200 for implantation within the left atrial appendage 50. The occlusive medical implant 200 may include the expandable framework 110, as described herein. In some embodiments, the expandable framework 110 may be configured to self-expand from the collapsed configuration (e.g., FIG. 6) to an expanded configuration (e.g., FIG. 7) when unconstrained. In at least some embodiments, the occlusive medical implant 200 may include the occlusive element 120, as described herein, disposed on the proximal portion 114 of the expandable framework 110. In some embodiments, at least a portion of the expandable framework 110 may be mechanically expandable from the expanded configuration (e.g., FIG. 7) to the securement configuration (e.g., FIG. 8). In some embodiments, a distal portion 116 of the expandable framework 110 may be mechanically expandable from the expanded configuration (e.g., FIG. 7) to the securement configuration (e.g., FIG. 8).

In some embodiments, when the occlusive medical implant 200 is disposed within the left atrial appendage 50, the expandable framework 110 and/or the distal portion 116 of the expandable framework 110 exerts a first radial force on the left atrial appendage 50 in the expanded configuration (e.g., FIG. 7) and the expandable framework 110 and/or the distal portion 116 of the expandable framework 110 exerts a second radial force on the left atrial appendage 50 in the securement configuration (e.g., FIG. 8). In at least some embodiments, the second radial force is greater than the first radial force. In some embodiments, the expandable framework 110 and/or the distal portion 116 of the expandable framework 110 may have a first radialmost outer extent in the expanded configuration (e.g., FIG. 7) and a second radialmost outer extent in the securement configuration (e.g., FIG. 8). In at least some embodiments, the second radialmost outer extent is greater than the first radialmost outer extent. By mechanically expanding at least a portion of the expandable framework 110 and/or the distal portion 116 of the expandable framework 110 to a greater radialmost outer extent than it can, does, or would expand to on its own, the expandable framework 110 and/or the distal portion 116 of the expandable framework 110 may exert greater radial force against the lateral wall 54 of the left atrial appendage 50, thereby achieving and/or improving securement and/or anchoring of the occlusive medical implant 200 within the left atrial appendage 50 without the need for radially extending anchoring elements piercing the lateral wall 54 of the left atrial appendage 50.

In some embodiments, the occlusive medical implant 200 may include the proximal hub 130 fixedly attached to the proximal end of the expandable framework 110. The occlusive medical implant 200 may include a distal hub 260 fixedly attached to the distal end of the expandable framework 110. The occlusive medical implant 200 may include a proximal beam 270 extending distally from the proximal hub 130 within an interior of the expandable framework 110.

The occlusive medical implant 200 may include a distal beam 280 extending proximally from the distal hub 260 within the interior of the expandable framework 110. The distal beam 280 may be engaged with the proximal beam 270. In some embodiments, the distal beam 280 may be also axially movable relative to the proximal beam 270. In some embodiments, the proximal beam 270 may be fixedly attached to the proximal hub 130. In some embodiments, the proximal beam 270 may be integrally and/or monolithically formed with the proximal hub 130.

In some embodiments, the distal beam 280 may be rotatable relative to the distal hub 260. In some embodiments, the distal hub 260 may include a central aperture 262. The distal beam 280 may extend through the central aperture 262. In some embodiments, the distal beam 280 may include a proximal portion 282, a distal neck 284 have a reduced diameter compared to the proximal portion 282, and a distal flange 286 disposed at and/or forming a distal end of the distal beam 280. The distal neck 284 may have an outer diameter less than a diameter of the central aperture 262. The distal neck 284 may be disposed in and/or may extend through the central aperture 262 of the distal hub 260. The distal neck 284 may be configured to rotate within the central aperture 262.

The distal flange 286 may be disposed distal of the distal hub 260. In some embodiments, the distal flange 286 may be disposed on an opposite side of the distal hub 260 from the proximal portion 282 of the distal beam 280. The distal flange 286 may have a radial extent greater than a radial extent of the distal neck 284 and greater than the diameter of the central aperture 262 of the distal hub 260. In some embodiments, the distal flange 286 may be fixedly attached, such as by welding or other means, to the distal neck 284 after inserting the distal neck 284 of the distal beam 280 through the central aperture 262. In some embodiments, the distal flange 286 may be formed after inserting the distal neck 284 of the distal beam 280 through the central aperture 262. Other configurations are also contemplated. In some embodiments, the distal hub 260 may be formed as multiple pieces that are fixedly attached to each other after disposing the distal neck 284 within the central aperture 262, such as by welding or other means. Other configurations are also contemplated.

In some embodiments, the distal beam 280 may be threadably and/or rotatably engaged with the proximal beam 270. In some embodiments, the proximal beam 270 may include internal threads 272 configured to engage with external threads 288 formed on the distal beam 280. In some embodiments, the distal beam 280 may be rotatable relative to the proximal beam 270. In some embodiments, rotation of the distal beam 280 may change an axial position of the distal hub 260 relative to the proximal hub 130. In some embodiments, rotation of the distal beam 280 in a first direction may move the distal hub 260 closer to the proximal hub 130. In some embodiments, rotation of the distal beam 280 in a second direction opposite the first direction may move the distal hub 260 farther away from the proximal hub 130.

The occlusive medical implant 200 may be releasably secured at and/or to the distal end of the core wire 30. In some embodiments, the distal end of the core wire 30 may extend into the proximal hub 130 and/or the distal beam 280. In some embodiments, the distal end of the core wire 30 may be engaged with the proximal portion 282 of the distal beam 280.

In some embodiments, the medical device system 10 may include a locking pin 290 engaged with the occlusive medical implant 200 and the core wire 30. In some embodiments, the locking pin 290 may be engaged with the distal beam 280 and the core wire 30. In some embodiments, the locking pin 290 may extend transversely to a longitudinal axis of the core wire 30. Other configurations are also contemplated. In some embodiments, the locking pin 290 may nonrotatably secure the core wire 30 to the occlusive medical implant 200 and/or the distal beam 280. In some embodiments, as the core wire 30 is rotated, the distal beam 280 may rotate relative to the proximal beam 270 and/or the distal hub 260. In some embodiments, rotation of the distal beam 280 relative to the proximal beam 270 and/or the distal hub 260 may move the distal beam 280 distally relative to the proximal beam 270 and/or the proximal hub 130. Rotation of the distal beam 280 relative to the proximal beam 270 and/or the distal hub 260 may mechanically expand the expandable framework 110 from the expanded configuration (e.g., FIG. 7) to the securement configuration (e.g., FIG. 8) by shifting the distal beam 280 and/or the distal hub 260 distally from and/or with respect to the proximal hub 130, thereby causing at least a portion (e.g., the distal portion 116) of the expandable framework 110 to expand radially outward to the securement configuration.

In some embodiments, the medical device system 10 may include a pull wire 292 fixed to the locking pin 290 and extending proximally from the occlusive medical implant 200. In at least some embodiments, the pull wire 292 may extend alongside the core wire 30. The pull wire 292 may be configured to disengage the locking pin 290 from the occlusive medical implant 200 (and/or the distal beam 280) and the core wire 30 to release the occlusive medical implant 200 from the core wire 30. Upon disengaging the locking pin 290 from the occlusive medical implant 200, the distal beam 280, and/or the core wire 30, the core wire 30 may be proximally retracted from the occlusive medical implant 200 and/or the distal beam 280 to leave the occlusive medical implant 200 implanted within the left atrial appendage 50.

Figure 9:
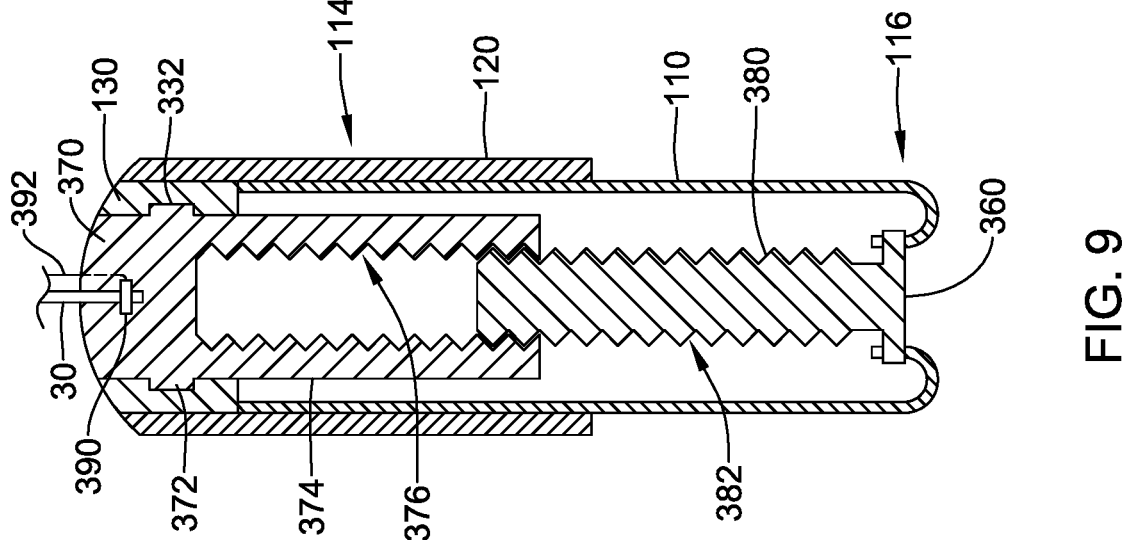
FIGS. 9-10 are partial cross-sectional views illustrating selected aspects of an alternative configuration of the implant of FIGS. 4-5.
Figure 9:
Figure 10:
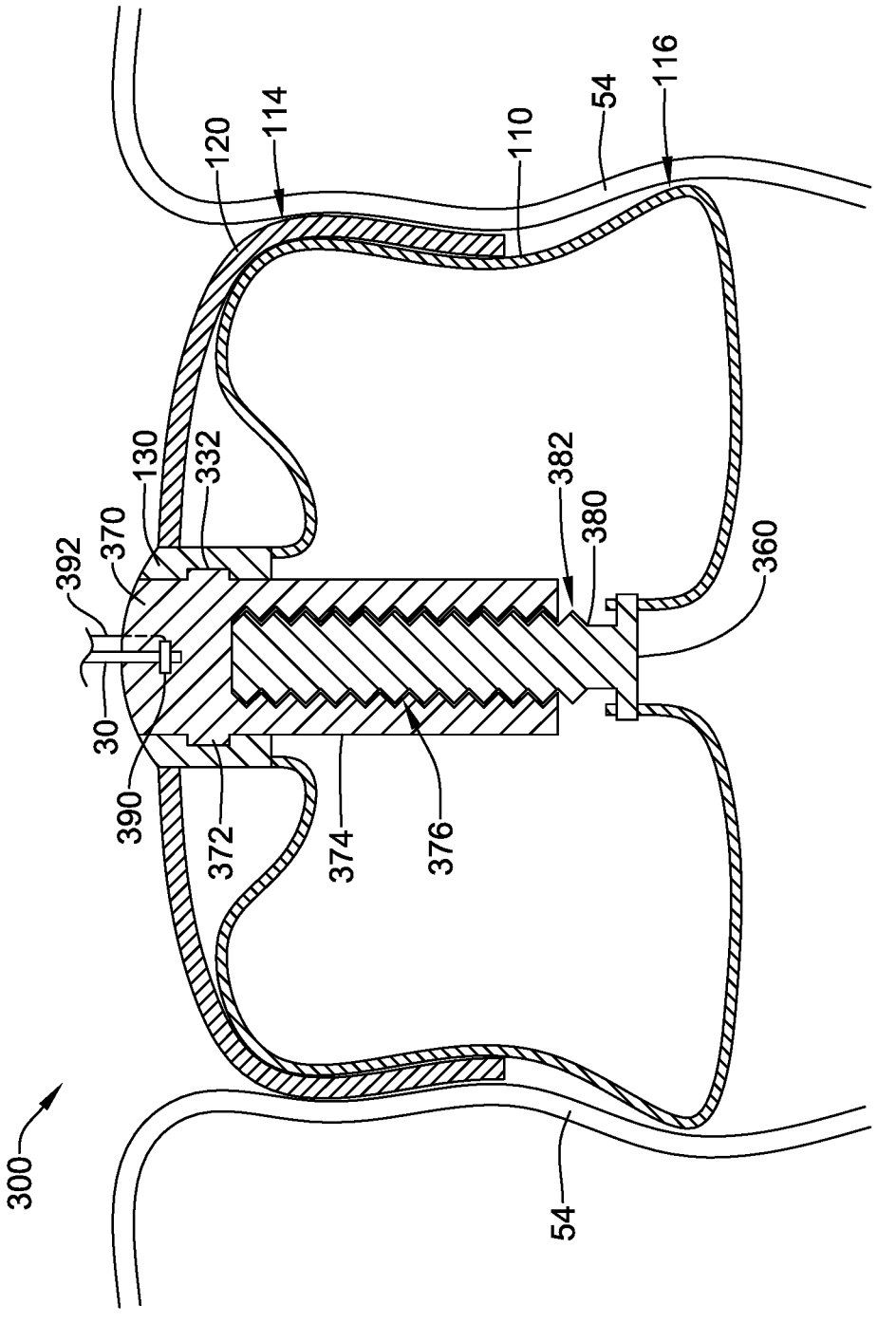

FIGS. 9-10 illustrate selected aspects of another example embodiment of an occlusive medical implant 300 for implantation within the left atrial appendage 50. The occlusive medical implant 300 may include the expandable framework 110, as described herein. In some embodiments, the expandable framework 110 may be configured to self-expand from the collapsed configuration (e.g., FIG. 9) to an expanded configuration when unconstrained. In at least some embodiments, the occlusive medical implant 300 may include the occlusive element 120, as described herein, disposed on the proximal portion 114 of the expandable framework 110. In some embodiments, at least a portion of the expandable framework 110 may be mechanically expandable from the expanded configuration to the securement configuration (e.g., FIG. 10). In some embodiments, a distal portion 116 of the expandable framework 110 may be mechanically expandable from the expanded configuration to the securement configuration (e.g., FIG. 10).

In some embodiments, when the occlusive medical implant 300 is disposed within the left atrial appendage 50, the expandable framework 110 and/or the distal portion 116 of the expandable framework 110 exerts a first radial force on the left atrial appendage 50 in the expanded configuration and the expandable framework 110 and/or the distal portion 116 of the expandable framework 110 exerts a second radial force on the left atrial appendage 50 in the securement configuration (e.g., FIG. 10). In at least some embodiments, the second radial force is greater than the first radial force. In some embodiments, the expandable framework 110 and/or the distal portion 116 of the expandable framework 110 may have a first radialmost outer extent in the expanded configuration and a second radialmost outer extent in the securement configuration (e.g., FIG. 10). In at least some embodiments, the second radialmost outer extent is greater than the first radialmost outer extent. By mechanically expanding at least a portion of the expandable framework 110 and/or the distal portion 116 of the expandable framework 110 to a greater radialmost outer extent than it can, does, or would expand to on its own, the expandable framework 110 and/or the distal portion 116 of the expandable framework 110 may exert greater radial force against the lateral wall 54 of the left atrial appendage 50, thereby improving securement and/or anchoring of the occlusive medical implant 300 within the left atrial appendage 50 without the need for radially extending anchoring elements piercing the lateral wall 54 of the left atrial appendage 50.

In some embodiments, the occlusive medical implant 300 may include the proximal hub 130 fixedly attached to the proximal end of the expandable framework 110. The occlusive medical implant 300 may include a distal hub 360 fixedly attached to the distal end of the expandable framework 110. The occlusive medical implant 300 may include a proximal beam 370 extending distally from the proximal hub 130 within an interior of the expandable framework 110. The occlusive medical implant 300 may include a distal beam 380 extending proximally from the distal hub 360 within the interior of the expandable framework 110. In some embodiments, the distal beam 380 may be fixedly attached to and/or nonrotatable relative to the distal hub 360. The distal beam 380 may be engaged with the proximal beam 370. In some embodiments, the distal beam 380 may be axially movable relative to the proximal beam 370.

In some embodiments, the proximal beam 370 may be axially fixed relative to the proximal hub 130. In some embodiments, the proximal beam 370 may be rotatable relative to the proximal hub 130 and/or the distal beam 380. In some embodiments, the proximal beam 370 may include a proximal flange 372 extending radially outward from a body 374 of the proximal beam 370. In some embodiments, the proximal hub 130 may include a channel 332 formed in an inner surface of the proximal hub 130. In some embodiments, the channel 332 may open radially inward toward a central longitudinal axis of the proximal hub 130 and/or the expandable framework 110. The channel 332 may extend circumferentially around the central longitudinal axis. In some embodiments, the proximal flange 372 of the proximal beam 370 may be disposed within the channel 332 of the proximal hub 130. In some embodiments, the proximal hub 130 may be formed as multiple pieces that are fixedly attached to each other after disposing the proximal flange 372 within the channel 332, such as by welding or other means. Other configurations are also contemplated.

In some embodiments, a distal portion of the body 374 of the proximal beam 370 may be hollow and/or tubular. The distal portion of the body 374 may be configured to receive the distal beam 380 therein. In some embodiments, the distal portion of the body 374 may include internal threads 376 and the distal beam 380 may include external threads 382. In some embodiments, the distal beam 380 may be threadably and/or rotatably engaged with the proximal beam 370.

In some embodiments, the proximal beam 370 may be rotatable relative to the distal beam 380. In some embodiments, rotation of the proximal beam 370 may change an axial position of the distal hub 360 relative to the proximal hub 130. In some embodiments, rotation of the proximal beam 370 in a first direction may move the distal hub 360 closer to the proximal hub 130. In some embodiments, rotation of the proximal beam 370 in a second direction opposite the first direction may move the distal hub 360 farther away from the proximal hub 130.

The occlusive medical implant 300 may be releasably secured at and/or to the distal end of the core wire 30. In some embodiments, the distal end of the core wire 30 may extend into the proximal hub 130 and/or the proximal beam 370. In some embodiments, the distal end of the core wire 30 may be engaged with the proximal beam 370.

In some embodiments, the medical device system 10 may include a locking pin 390 engaged with the occlusive medical implant 300 and the core wire 30. In some embodiments, the locking pin 390 may be engaged with the proximal beam 370 and the core wire 30. In some embodiments, the locking pin 390 may extend transversely to a longitudinal axis of the core wire 30. Other configurations are also contemplated. In some embodiments, the locking pin 390 may nonrotatably secure the core wire 30 to the occlusive medical implant 300 and/or the proximal beam 370. In some embodiments, as the core wire 30 is rotated, the proximal beam 370 may rotate relative to the distal beam 380 and/or the proximal hub 130. In some embodiments, rotation of the proximal beam 370 relative to the distal beam 380 may move the distal beam 380 and/or the distal hub 360 proximally relative to the proximal beam 370 and/or the proximal hub 130. Rotation of the proximal beam 370 relative to the distal beam 380 may mechanically expand the expandable framework 110 from the expanded configuration to the securement configuration (e.g., FIG. 10) by shifting the distal beam 380 and/or the distal hub 360 proximally toward and/or with respect to the proximal hub 130, thereby causing at least a portion (e.g., the distal portion 116) of the expandable framework 110 to expand radially outward to the securement configuration.

In some embodiments, the medical device system 10 may include a pull wire 392 fixed to the locking pin 390 and extending proximally from the occlusive medical implant 300. In at least some embodiments, the pull wire 392 may extend alongside the core wire 30. The pull wire 392 may be configured to disengage the locking pin 390 from the occlusive medical implant 300 (and/or the proximal beam 370) and the core wire 30 to release the occlusive medical implant 300 from the core wire 30. Upon disengaging the locking pin 390 from the occlusive medical implant 300, the proximal beam 370, and/or the core wire 30, the core wire 30 may be proximally retracted from the occlusive medical implant 300 and/or the proximal beam 370 to leave the occlusive medical implant 300 implanted within the left atrial appendage 50.

Figure 11:
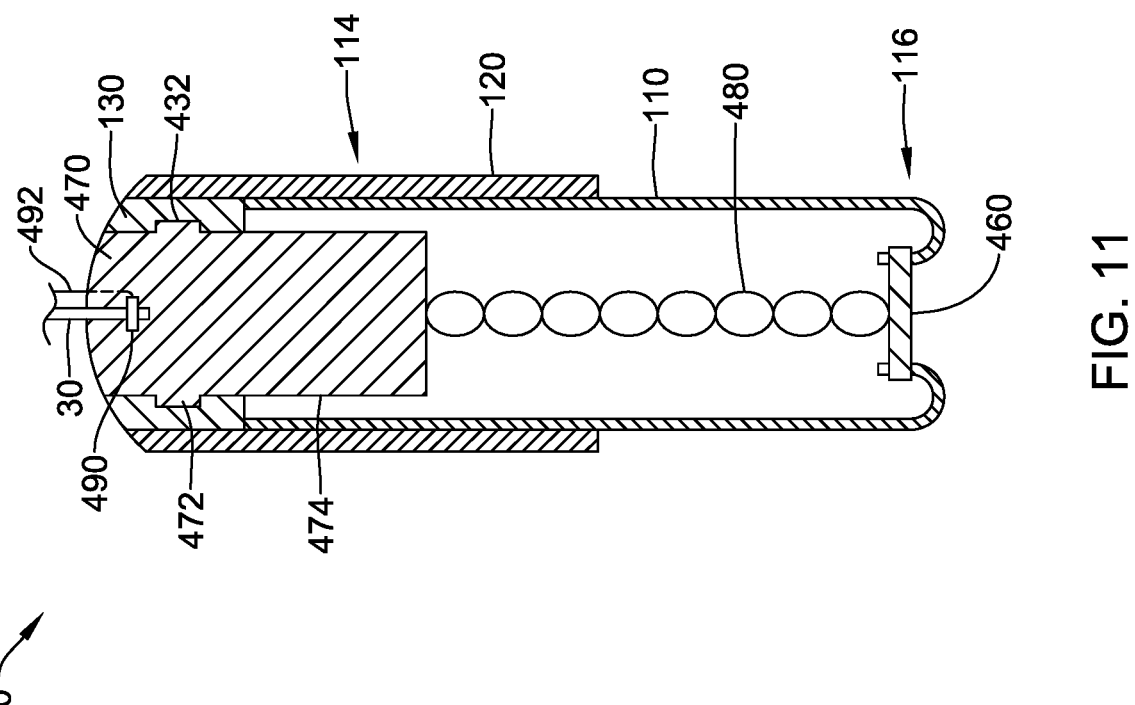
FIGS. 11-12 are partial cross-sectional views illustrating selected aspects of an alternative configuration of the implant of FIGS. 4-5.
Figure 12:
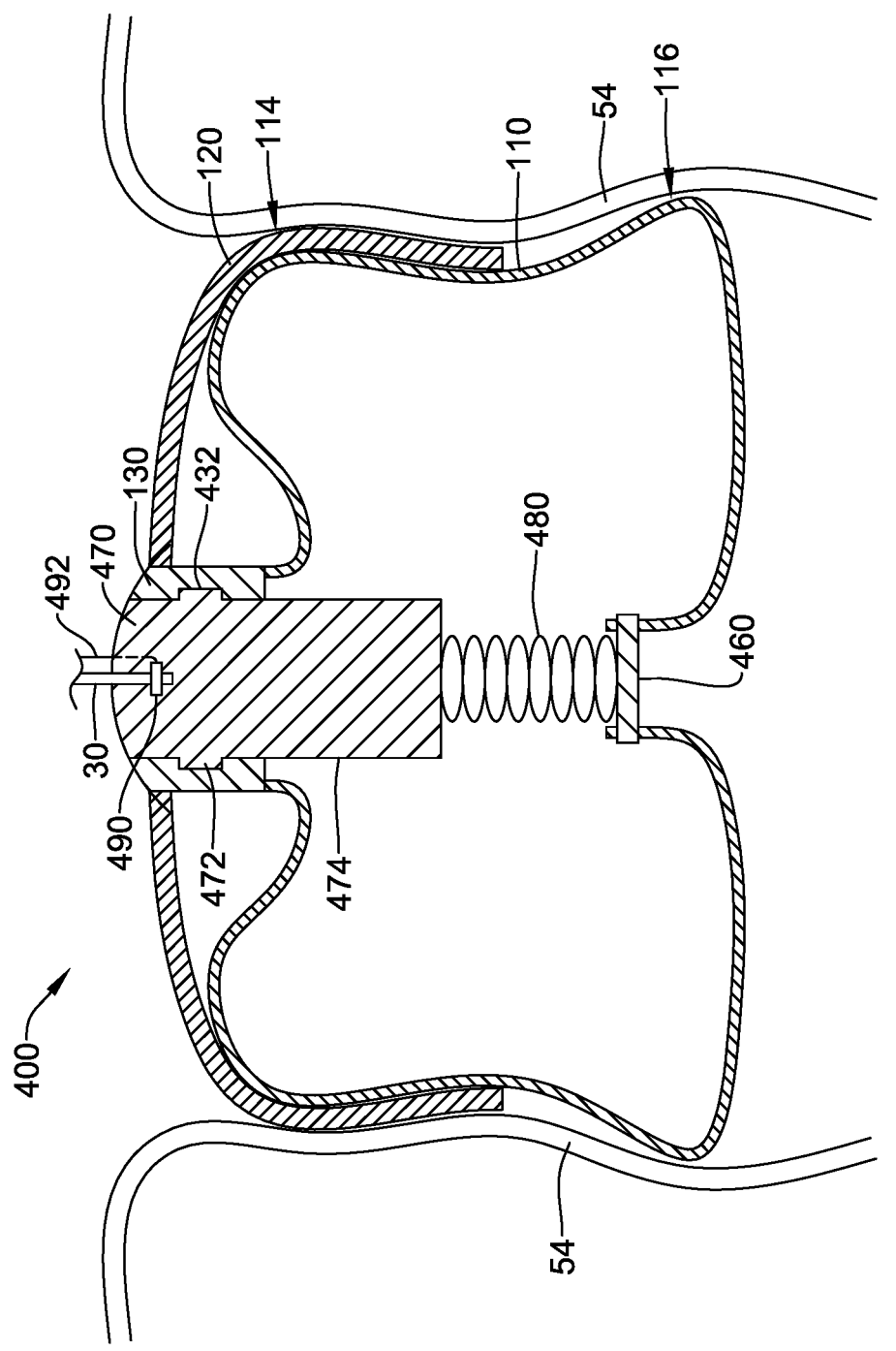

FIGS. 11-12 illustrate selected aspects of another example embodiment of an occlusive medical implant 400 for implantation within the left atrial appendage 50. The occlusive medical implant 400 may include the expandable framework 110, as described herein. In some embodiments, the expandable framework 110 may be configured to self-expand from the collapsed configuration (e.g., FIG. 11) to an expanded configuration when unconstrained. In at least some embodiments, the occlusive medical implant 400 may include the occlusive element 120, as described herein, disposed on the proximal portion 114 of the expandable framework 110. In some embodiments, at least a portion of the expandable framework 110 may be mechanically expandable from the expanded configuration to the securement configuration (e.g., FIG. 12). In some embodiments, a distal portion 116 of the expandable framework 110 may be mechanically expandable from the expanded configuration to the securement configuration (e.g., FIG. 12).

In some embodiments, when the occlusive medical implant 400 is disposed within the left atrial appendage 50, the expandable framework 110 and/or the distal portion 116 of the expandable framework 110 exerts a first radial force on the left atrial appendage 50 in the expanded configuration and the expandable framework 110 and/or the distal portion 116 of the expandable framework 110 exerts a second radial force on the left atrial appendage 50 in the securement configuration (e.g., FIG. 12). In at least some embodiments, the second radial force is greater than the first radial force. In some embodiments, the expandable framework 110 and/or the distal portion 116 of the expandable framework 110 may have a first radialmost outer extent in the expanded configuration and a second radialmost outer extent in the securement configuration (e.g., FIG. 12). In at least some embodiments, the second radialmost outer extent is greater than the first radialmost outer extent. By mechanically expanding at least a portion of the expandable framework 110 and/or the distal portion 116 of the expandable frame-work 110 to a greater radialmost outer extent than it can, does, or would expand to on its own, the expandable framework 110 and/or the distal portion 116 of the expand-able framework 110 may exert greater radial force against the lateral wall 54 of the left atrial appendage 50, thereby improving securement and/or anchoring of the occlusive medical implant 400 within the left atrial appendage 50 without the need for radially extending anchoring elements piercing the lateral wall 54 of the left atrial appendage 50.

In some embodiments, the occlusive medical implant 400 may include the proximal hub 130 fixedly attached to the proximal end of the expandable framework 110. The occlu-sive medical implant 400 may include a distal hub 460 fixedly attached to the distal end of the expandable frame-work 110. The occlusive medical implant 400 may include a proximal beam 470 extending distally from the proximal hub 130 within an interior of the expandable framework 110. The occlusive medical implant 400 may include a distal beam 480 extending proximally from the distal hub 460 within the interior of the expandable framework 110. In some embodiments, the distal beam 480 may be fixedly attached to the distal hub 460. The distal beam 480 may be engaged with the proximal beam 470. In some embodi-ments, the distal beam 480 may be fixedly attached to the proximal beam 470. In some embodiments, at least a portion of the distal beam 480 may be axially movable relative to the proximal beam 470.

In some embodiments, the proximal beam 470 may be axially fixed relative to the proximal hub 130. In some embodiments, the proximal beam 470 may be rotatable relative to the proximal hub 130. In some embodiments, the proximal beam 470 may include a proximal flange 472 extending radially outward from a body 474 of the proximal beam 470. In some embodiments, the proximal hub 130 may include a channel 432 formed in an inner surface of the proximal hub 130. In some embodiments, the channel 432 may open radially inward toward a central longitudinal axis of the proximal hub 130 and/or the expandable framework 110. The channel 432 may extend circumferentially around the central longitudinal axis. In some embodiments, the proximal flange 472 of the proximal beam 470 may be disposed within the channel 432 of the proximal hub 130. In some embodiments, the proximal hub 130 may be formed as multiple pieces that are fixedly attached to each other after disposing the proximal flange 472 within the channel 432, such as by welding or other means. Other configurations are also contemplated.

In some embodiments, the distal beam 480 may be a coil spring. In some embodiments, rotation of the proximal beam 470 may change an axial position of the distal hub 460 relative to the proximal hub 130. In some embodiments, rotation of the proximal beam 470 may tighten the coil spring by bringing adjacent coils closer together. As such, rotation of the proximal beam 470 in a first direction may move the distal hub 460 closer to the proximal hub 130. In some embodiments, rotation of the proximal beam 470 may loosen the coil spring and permit adjacent coils to space farther apart. As such, rotation of the proximal beam 470 in a second direction opposite the first direction may move the distal hub 460 farther away from the proximal hub 130.

The occlusive medical implant 400 may be releasably secured at and/or to the distal end of the core wire 30. In some embodiments, the distal end of the core wire 30 may extend into the proximal hub 130 and/or the proximal beam 470. In some embodiments, the distal end of the core wire 30 may be engaged with the proximal beam 470.

In some embodiments, the medical device system 10 may include a locking pin 490 engaged with the occlusive medical implant 400 and the core wire 30. In some embodi-ments, the locking pin 490 may be engaged with the proximal beam 470 and the core wire 30. In some embodi-ments, the locking pin 490 may extend transversely to a longitudinal axis of the core wire 30. Other configurations are also contemplated. In some embodiments, the locking pin 490 may nonrotatably secure the core wire 30 to the occlusive medical implant 400 and/or the proximal beam 470. In some embodiments, as the core wire 30 is rotated, the proximal beam 470 may rotate relative to the proximal hub 130. In some embodiments, rotation of the proximal beam 470 may move at least a portion of the distal beam 480 and/or the distal hub 460 proximally relative to the proximal beam 470 and/or the proximal hub 130. Rotation of the proximal beam 470 may mechanically expand the expand-able framework 110 from the expanded configuration to the securement configuration (e.g., FIG. 12) by shifting at least a portion of the distal beam 480 and/or the distal hub 460 proximally toward and/or with respect to the proximal hub 130, thereby causing at least a portion (e.g., the distal portion 116) of the expandable framework 110 to expand radially outward to the securement configuration.

In some embodiments, the medical device system 10 may include a pull wire 492 fixed to the locking pin 490 and extending proximally from the occlusive medical implant 400. In at least some embodiments, the pull wire 492 may extend alongside the core wire 30. The pull wire 492 may be configured to disengage the locking pin 490 from the occlusive medical implant 400 (and/or the proximal beam 470) and the core wire 30 to release the occlusive medical implant 400 from the core wire 30. Upon disengaging the locking pin 490 from the occlusive medical implant 400, the proximal beam 470, and/or the core wire 30, the core wire 30 may be proximally retracted from the occlusive medical implant 400 and/or the proximal beam 470 to leave the occlusive medical implant 400 implanted within the left atrial appendage 50.

Figure 13:
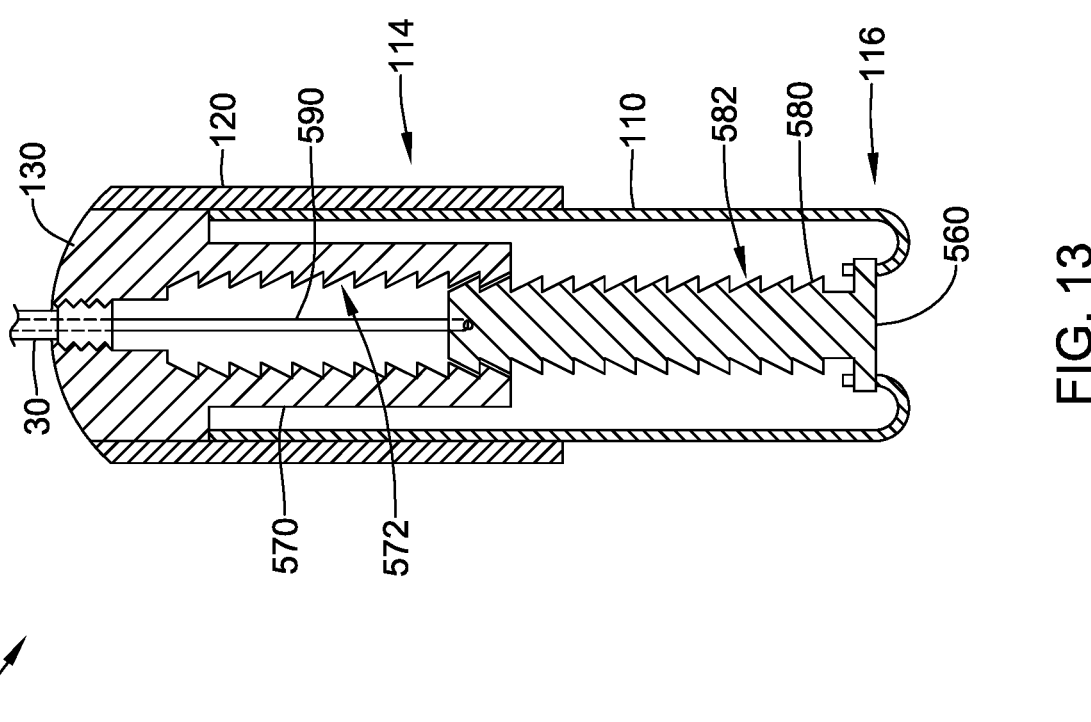
FIGS. 13-14 are partial cross-sectional views illustrating selected aspects of an alternative configuration of the implant of FIGS. 4-5.
Figure 14:
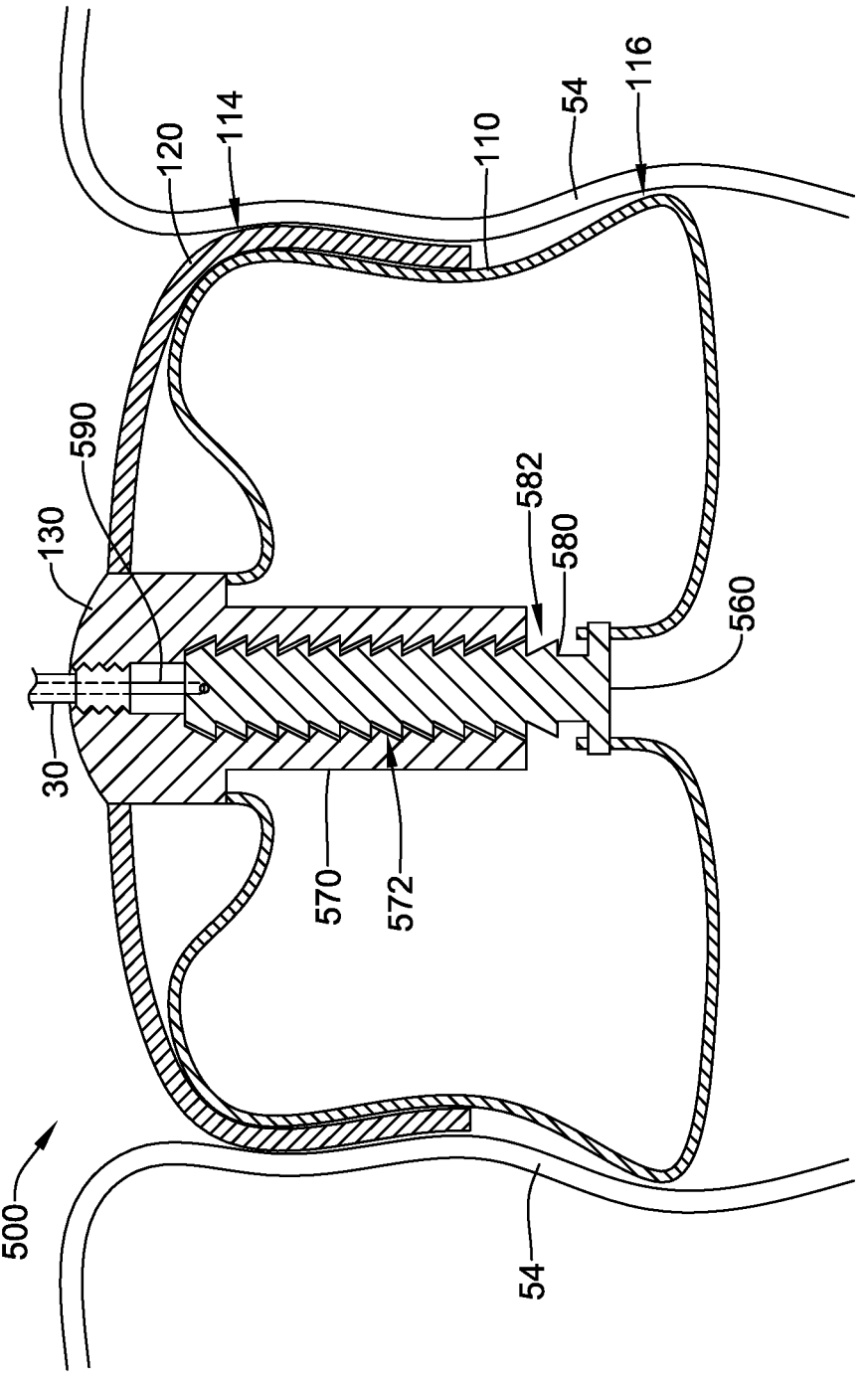

FIGS. 13-14 illustrate selected aspects of another example embodiment of an occlusive medical implant 500 for implantation within the left atrial appendage 50. The occlu-sive medical implant 500 may include the expandable framework 110, as described herein. In some embodiments, the expandable framework 110 may be configured to self-expand from the collapsed configuration (e.g., FIG. 13) to an expanded configuration when unconstrained. In at least some embodiments, the occlusive medical implant 500 may include the occlusive element 120, as described herein, disposed on the proximal portion 114 of the expandable framework 110. In some embodiments, at least a portion of the expandable framework 110 may be mechanically expandable from the expanded configuration to the secure- ment configuration (e.g., FIG. 14). In some embodiments, a distal portion 116 of the expandable framework 110 may be mechanically expandable from the expanded configuration to the securement configuration (e.g., FIG. 14).

In some embodiments, when the occlusive medical implant 500 is disposed within the left atrial appendage 50, the expandable framework 110 and/or the distal portion 116 of the expandable framework 110 exerts a first radial force on the left atrial appendage 50 in the expanded configuration and the expandable framework 110 and/or the distal portion 116 of the expandable framework 110 exerts a second radial force on the left atrial appendage 50 in the securement configuration (e.g., FIG. 14). In at least some embodiments, the second radial force is greater than the first radial force. In some embodiments, the expandable framework 110 and/ or the distal portion 116 of the expandable framework 110 may have a first radialmost outer extent in the expanded configuration and a second radialmost outer extent in the securement configuration (e.g., FIG. 14). In at least some embodiments, the second radialmost outer extent is greater than the first radialmost outer extent. By mechanically expanding at least a portion of the expandable framework 110 and/or the distal portion 116 of the expandable frame- work 110 to a greater radialmost outer extent than it can, does, or would expand to on its own, the expandable framework 110 and/or the distal portion 116 of the expand- able framework 110 may exert greater radial force against the lateral wall 54 of the left atrial appendage 50, thereby improving securement and/or anchoring of the occlusive medical implant 500 within the left atrial appendage 50 without the need for radially extending anchoring elements piercing the lateral wall 54 of the left atrial appendage 50.

In some embodiments, the occlusive medical implant 500 may include the proximal hub 130 fixedly attached to the proximal end of the expandable framework 110. The occlu- sive medical implant 500 may include a distal hub 560 fixedly attached to the distal end of the expandable frame- work 110. The occlusive medical implant 500 may include a proximal beam 570 extending distally from the proximal hub 130 within an interior of the expandable framework 110. The occlusive medical implant 500 may include a distal beam 580 extending proximally from the distal hub 560 within the interior of the expandable framework 110. In some embodiments, the distal beam 580 may be fixedly attached to and/or nonrotatable relative to the distal hub 560. The distal beam 580 may be engaged with the proximal beam 570. In some embodiments, the distal beam 580 may be axially movable relative to the proximal beam 570.

In some embodiments, the proximal beam 570 may be axially fixed relative to the proximal hub 130. In some embodiments, the proximal beam 570 may be fixedly attached to the proximal hub 130. In some embodiments, the proximal beam 570 may be integrally and/or monolithically formed with the proximal hub 130.

In some embodiments, a distal portion of the proximal beam 570 may be hollow and/or tubular. The distal portion of the proximal beam 570 may be configured to receive the distal beam 580 therein. In some embodiments, the proximal beam 570 may include a plurality of internal flanges 572 extending radially inward from the proximal beam 570. The plurality of internal flanges 572 may each include a distal face that is tapered radially inward and proximally and/or toward the proximal hub 130. In some embodiments, the plurality of internal flanges 572 may each include a sub- stantially flat and/or horizontal proximal face. Other con- figurations are also contemplated. The distal beam 580 may include a plurality of external flanges 582 extending radially outward from the distal beam 580. The plurality of external flanges 582 may each include a proximal face that is tapered radially inward and proximally and/or toward the proximal hub 130. In some embodiments, the plurality of external flanges 582 may each include a substantially flat and/or horizontal distal face. Other configurations are also contem- plated.

In some embodiments, the plurality of internal flanges 572 and the plurality of external flanges 582 may combine to form a ratcheting-type mechanism that permits movement of the distal beam 580 relative to the proximal beam 570 in a first direction (e.g., in a proximal direction) and prevents movement of the distal beam 580 relative to the proximal beam 570 in a second direction opposite the first direction (e.g., in a distal direction). In at least some embodiments, the plurality of internal flanges 572 may be configured to deflect and/or the plurality of external flanges 582 may be config- ured to deflect when the plurality of internal flanges 572 engages the plurality of external flanges 582 as the distal beam 580 is moved proximally relative to the proximal beam 570 (e.g., as a proximally directed force is applied to the distal beam 580). Accordingly, the distal beam 580 may be configured to move proximally relative to the proximal beam 570 and the plurality of internal flanges 572 and the plurality of external flanges 582 may be configured to allow or permit proximal movement of the distal beam 580 relative to the proximal beam 570. The plurality of internal flanges 572 may be configured to resist and/or prevent deflection and/or the plurality of external flanges 582 may be config- ured to resist and/or prevent deflection when the plurality of internal flanges 572 engages the plurality of external flanges 582 as the distal beam 580 is moved distally relative to the proximal beam 570 (e.g., as a distally directed force is applied to the distal beam 580). Accordingly, the plurality of internal flanges 572 and the plurality of external flanges 582 may be configured to prevent distal movement of the distal beam 580 relative to the proximal beam 570.

In one alternative configuration, the proximal beam 570 may include the plurality of internal flanges 572, as seen in FIGS. 13-14, and the distal beam 580 may include one or more external flanges, each having proximal and/or distal faces as described herein with respect to the plurality of external flanges 582, extending radially outward from the distal beam 580. In some embodiments, the distal beam 580 may include only one external flange extending radially outward from the distal beam 580. In some embodiments, the only one external flange may be disposed at a free end (e.g., a proximal end) of the distal beam 580 opposite the distal hub 560 and/or the only one external flange may be disposed in engagement with the proximal beam 570. In some embodiments, the distal beam 580 may include more than one external flange extending radially outward from the distal beam 580.

In another alternative configuration, the distal beam 580 may include the plurality of external flanges 582 extending radially outward from the distal beam 580, and the proximal beam 570 may include one or more internal flanges, each having proximal and/or distal faces as described herein with respect to the plurality of internal flanges 572, extending radially inward from the proximal beam 570. In some embodiments, the proximal beam 570 may include only one internal flange extending radially inward from the proximal beam 570. In some embodiments, the only one internal flange may be disposed at a free end (e.g., a distal end) of the proximal beam 570 opposite the proximal hub 130 and/or the only one internal flange may be disposed in engagement with the distal beam 580. In some embodiments, the proximal beam 570 may include more than one internal flange extending radially inward from the proximal beam 570.

The occlusive medical implant 500 may be releasably secured at and/or to the distal end of the core wire 30. In some embodiments, the distal end of the core wire 30 may extend into the proximal hub 130. In some embodiments, the distal end of the core wire 30 may be engaged with the proximal hub 130. In some embodiments, the distal end of the core wire 30 may be threadably and/or rotatably engaged with the proximal hub 130.

In some embodiments, the medical device system 10 may include a pull wire 590 slidably disposed within the core wire 30. The pull wire 590 may extend axially within and/or through the proximal beam 570 and engage with a proximal end of the distal beam 580. The pull wire 590 may extend to a proximal portion and/or a proximal end of the medical device system 10 and/or the catheter 40, where the pull wire 590 may be manipulated by a user. For example, after the occlusive medical implant 500 has been deployed from the lumen 42 of the catheter 40 and has self-expanded to the expanded configuration at a treatment site, the pull wire 590 may be pulled proximally to axially translate the distal beam 580 in a proximal direction relative to the proximal beam 570. Axial translation of the distal beam 580 in the proximal direction relative to the proximal beam 570 may mechanically expand the expandable framework 110 from the expanded configuration to the securement configuration (e.g., FIG. 14) by shifting the distal beam 580 and/or the distal hub 560 proximally toward and/or with respect to the proximal hub 130, thereby causing at least a portion (e.g., the distal portion 116) of the expandable framework 110 to expand radially outward to the securement configuration.

After mechanically expanding the expandable framework 110 to the securement configuration, the pull wire 590 may be pulled through the distal beam 580 and withdrawn from the occlusive medical implant 500 by releasing a first end of the pull wire 590 and pulling on a second end of the pull wire 590. Subsequently, the core wire 30 may be rotated relative to the proximal hub 130 to disengage the core wire 30 from the occlusive medical implant 500 and/or the proximal hub 130, and the core wire 30 may be proximally retracted from the occlusive medical implant 500 and/or the proximal hub 130 to leave the occlusive medical implant 500 implanted within the left atrial appendage 50.

Figure 15:
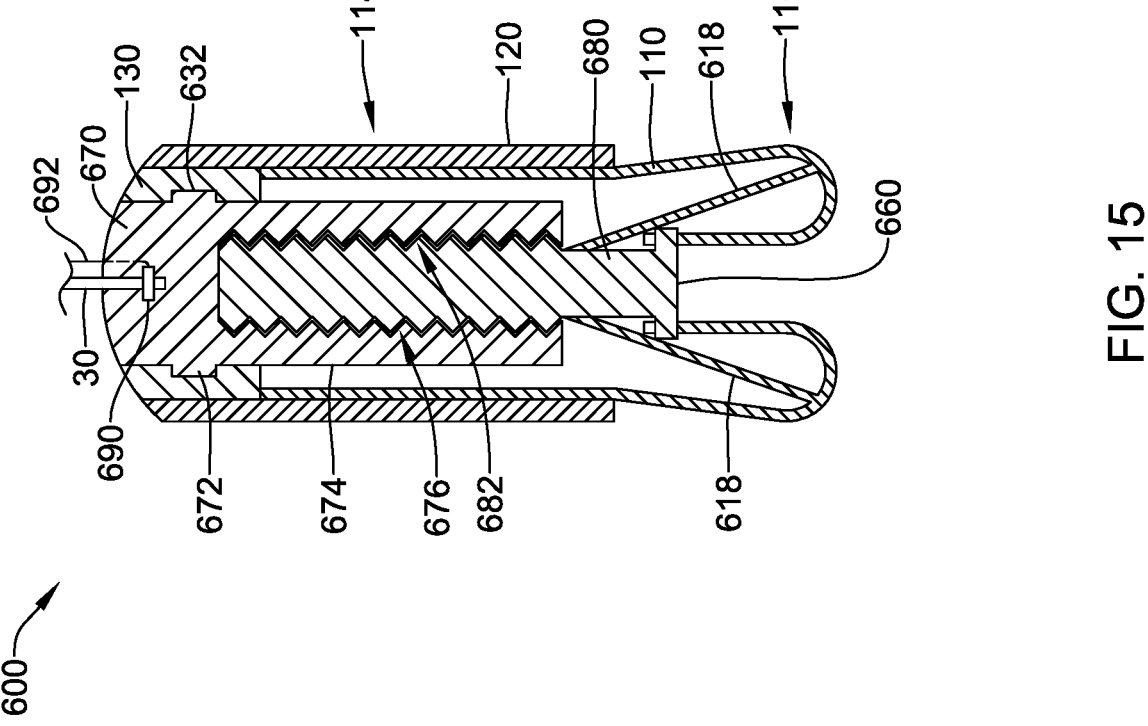
FIGS. 15-17 are partial cross-sectional views illustrating selected aspects of an alternative configuration of the implant of FIGS. 4-5.
Figure 16:
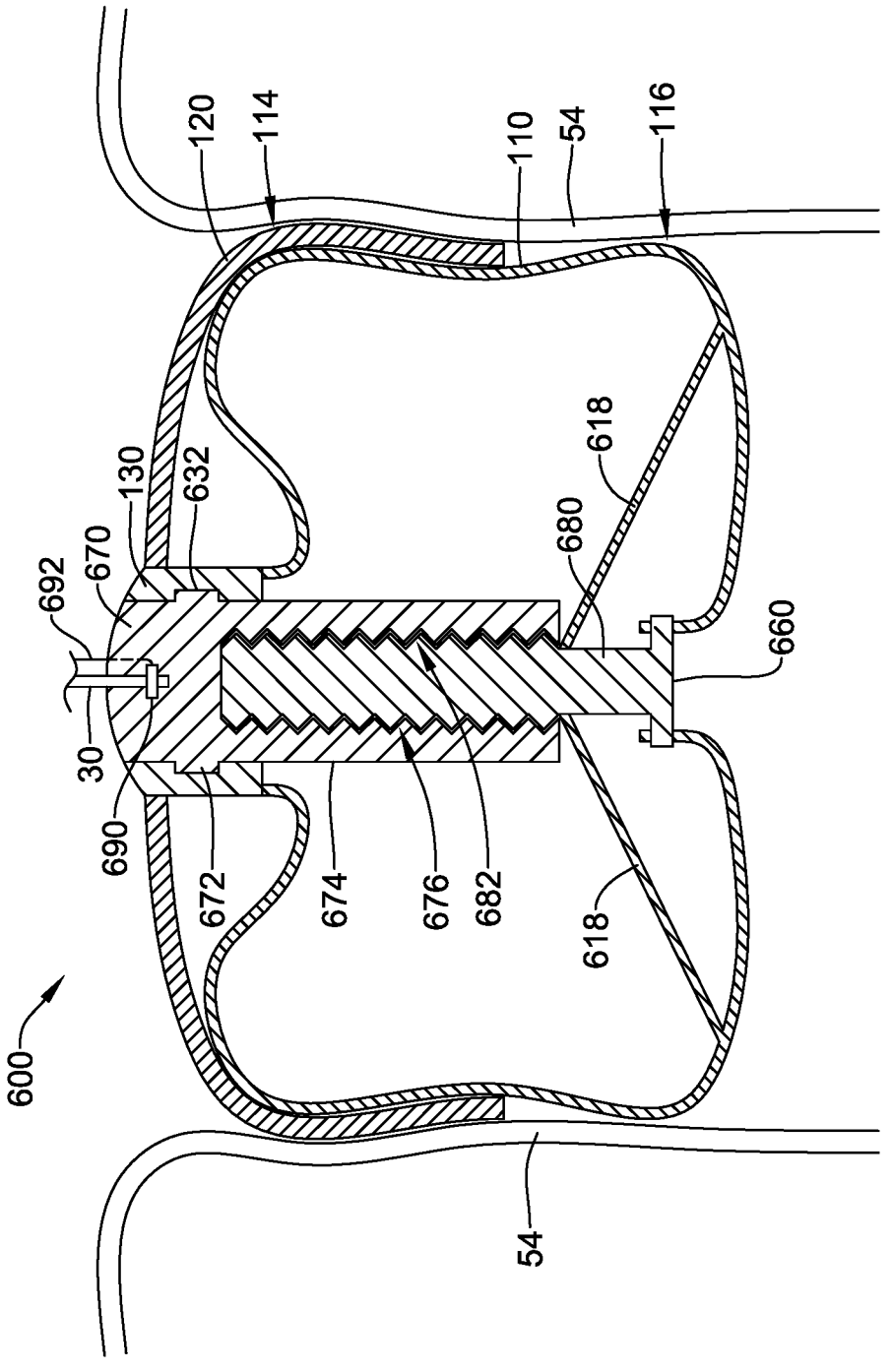
Figure 17:
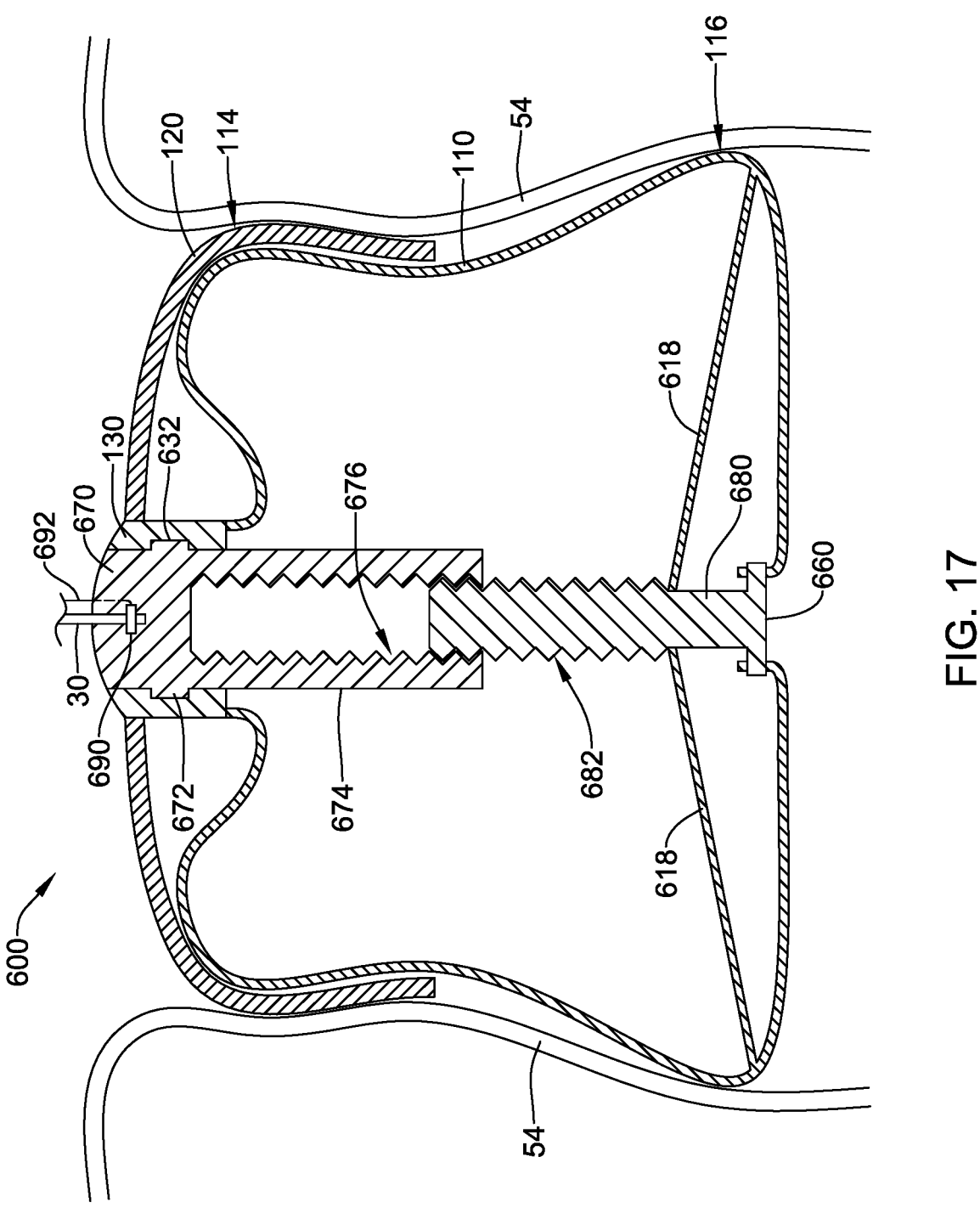

FIGS. 15-17 illustrate selected aspects of another example embodiment of an occlusive medical implant 600 for implantation within the left atrial appendage 50. The occlusive medical implant 600 may include the expandable framework 110, as described herein. In some embodiments, the expandable framework 110 may be configured to self-expand from the collapsed configuration (e.g., FIG. 15) to an expanded configuration (e.g., FIG. 16) when unconstrained. In at least some embodiments, the occlusive medical implant 600 may include the occlusive element 120, as described herein, disposed on the proximal portion 114 of the expandable framework 110. In some embodiments, at least a portion of the expandable framework 110 may be mechanically expandable from the expanded configuration (e.g., FIG. 16) to the securement configuration (e.g., FIG. 17). In some embodiments, a distal portion 116 of the expandable framework 110 may be mechanically expandable from the expanded configuration (e.g., FIG. 16) to the securement configuration (e.g., FIG. 17).

In some embodiments, when the occlusive medical implant 600 is disposed within the left atrial appendage 50, the expandable framework 110 and/or the distal portion 116 of the expandable framework 110 exerts a first radial force on the left atrial appendage 50 in the expanded configuration (e.g., FIG. 16) and the expandable framework 110 and/or the distal portion 116 of the expandable framework 110 exerts a second radial force on the left atrial appendage 50 in the securement configuration (e.g., FIG. 17). In at least some embodiments, the second radial force is greater than the first radial force. In some embodiments, the expandable framework 110 and/or the distal portion 116 of the expandable framework 110 may have a first radialmost outer extent in the expanded configuration (e.g., FIG. 16) and a second radialmost outer extent in the securement configuration (e.g., FIG. 17). In at least some embodiments, the second radialmost outer extent is greater than the first radialmost outer extent. By mechanically expanding at least a portion of the expandable framework 110 and/or the distal portion 116 of the expandable framework 110 to a greater radialmost outer extent than it can, does, or would expand to on its own, the expandable framework 110 and/or the distal portion 116 of the expandable framework 110 may exert greater radial force against the lateral wall 54 of the left atrial appendage 50, thereby improving securement and/or anchoring of the occlusive medical implant 300 within the left atrial appendage 50 without the need for radially extending anchoring elements piercing the lateral wall 54 of the left atrial appendage 50.

In some embodiments, the occlusive medical implant 600 may include the proximal hub 130 fixedly attached to the proximal end of the expandable framework 110. The occlusive medical implant 600 may include a distal hub 660 fixedly attached to the distal end of the expandable framework 110. The occlusive medical implant 600 may include a proximal beam 670 extending distally from the proximal hub 130 within an interior of the expandable framework 110. The occlusive medical implant 600 may include a distal beam 680 extending proximally from the distal hub 660 within the interior of the expandable framework 110. In some embodiments, the distal beam 680 may be fixedly attached to and/or nonrotatable relative to the distal hub 660. The distal beam 680 may be engaged with the proximal beam 670. In some embodiments, the distal beam 680 may be axially movable relative to the proximal beam 670.

In some embodiments, the proximal beam 670 may be axially fixed relative to the proximal hub 130. In some embodiments, the proximal beam 670 may be rotatable relative to the proximal hub 130 and/or the distal beam 680. In some embodiments, the proximal beam 670 may include a proximal flange 672 extending radially outward from a body 674 of the proximal beam 670. In some embodiments, the proximal hub 130 may include a channel 632 formed in an inner surface of the proximal hub 130. In some embodiments, the channel 632 may open radially inward toward a central longitudinal axis of the proximal hub 130 and/or the expandable framework 110. The channel 632 may extend circumferentially around the central longitudinal axis. In some embodiments, the proximal flange 672 of the proximal beam 670 may be disposed within the channel 632 of the proximal hub 130. In some embodiments, the proximal hub 130 may be formed as multiple pieces that are fixedly attached to each other after disposing the proximal flange 672 within the channel 632, such as by welding or other means. Other configurations are also contemplated.

In some embodiments, a distal portion of the body 674 of the proximal beam 670 may be hollow and/or tubular. The distal portion of the body 674 may be configured to receive the distal beam 680 therein. In some embodiments, the distal portion of the body 674 may include internal threads 676 and the distal beam 680 may include external threads 682. In some embodiments, the distal beam 680 may be threadably engaged with the proximal beam 670.

In some embodiments, the proximal beam 670 may be rotatable relative to the distal beam 680. In some embodiments, rotation of the proximal beam 670 may change an axial position of the distal hub 660 relative to the proximal hub 130. In some embodiments, rotation of the proximal beam 670 in a first direction may move the distal hub 660 closer to the proximal hub 130. In some embodiments, rotation of the proximal beam 670 in a second direction opposite the first direction may move the distal hub 660 farther away from the proximal hub 130.

The occlusive medical implant 600 may be releasably secured at and/or to the distal end of the core wire 30. In some embodiments, the distal end of the core wire 30 may extend into the proximal hub 130 and/or the proximal beam 670. In some embodiments, the distal end of the core wire 30 may be engaged with the proximal beam 670.

In some embodiments, the medical device system 10 may include a locking pin 690 engaged with the occlusive medical implant 600 and the core wire 30. In some embodiments, the locking pin 690 may be engaged with the proximal beam 670 and the core wire 30. In some embodiments, the locking pin 690 may extend transversely to a longitudinal axis of the core wire 30. Other configurations are also contemplated. In some embodiments, the locking pin 690 may nonrotatably secure the core wire 30 to the occlusive medical implant 600 and/or the proximal beam 670. In some embodiments, as the core wire 30 is rotated, the proximal beam 670 may rotate relative to the distal beam 680 and/or the proximal hub 130. In some embodiments, rotation of the proximal beam 670 relative to the distal beam 680 may move the distal beam 680 and/or the distal hub 660 distally relative to the proximal beam 670 and/or the proximal hub 130. Rotation of the proximal beam 670 relative to the distal beam 680 may mechanically expand the expandable framework 110 from the expanded configuration (e.g., FIG. 16) to the securement configuration (e.g., FIG. 17) by shifting the distal beam 680 and/or the distal hub 660 distally from and/or with respect to the proximal hub 130, thereby causing at least a portion (e.g., the distal portion 116) of the expandable framework 110 to expand radially outward to the securement configuration.

In some embodiments, the occlusive medical implant 600 may include a plurality of support struts 618 extending distally and radially outward from the distal beam 680 to the expandable framework 110. In some embodiments, the plurality of support struts 618 may be hingedly connected to the distal beam 680 and/or the expandable framework 110. In some embodiments, the plurality of support struts 618 may be flexible connected to the distal beam 680 and/or the expandable framework 110. In some embodiments, the plurality of support struts 618 may be integrally formed with the expandable framework 110 and/or the plurality of interconnected struts 112 and later connected to the distal beam 680. In some embodiments, the plurality of support struts 618 may be integrally formed with the distal beam 680 and may contact and/or press against the distal portion 116 of the expandable framework 110 without being connected or attached (directly or indirectly) to the expandable framework 110. Other configurations are also contemplated.

In at least some embodiments, the plurality of support struts 618 may be generally rigid along their length. In some embodiments, the plurality of support struts 618 may be configured to mechanically expand the distal portion 116 of the expandable framework 110 as the distal beam 680 is translated distally relative to the proximal beam 670 and/or the proximal hub 130. As the distal beam 680 is moved distally, the plurality of support struts 618 may change orientation relative to the distal beam 680 to urge and/or move the distal portion 116 of the expandable framework 110 radially outward from the distal beam 680.

For example, in the collapsed configuration (e.g., FIG. 15), the plurality of support struts 618 may be oriented in a first orientation extending more distally than radially outward from the distal beam 680. In the expanded configuration (e.g., FIG. 16), the plurality of support struts 618 may be oriented in a second orientation extending more radially outward than distally from the distal beam 680. In the securement configuration (e.g., FIG. 17), the plurality of support struts 618 may be oriented in a third orientation extending even more radially outward than distally from the distal beam 680 than in the second orientation. In the second orientation, the plurality of support struts 618 may be oriented closer to perpendicular to the central longitudinal axis of the occlusive medical implant 600, the expandable framework 110, and/or the distal beam 680 than in the first orientation. In the third orientation, the plurality of support struts 618 may be oriented closer to perpendicular to the central longitudinal axis of the occlusive medical implant 600, the expandable framework 110, and/or the distal beam 680 than in the second orientation.

In some embodiments, the medical device system 10 may include a pull wire 692 fixed to the locking pin 690 and extending proximally from the occlusive medical implant 600. In at least some embodiments, the pull wire 392 may extend alongside the core wire 30. The pull wire 692 may be configured to disengage the locking pin 690 from the occlusive medical implant 600 (and/or the proximal beam 670) and the core wire 30 to release the occlusive medical implant 600 from the core wire 30. Upon disengaging the locking pin 690 from the occlusive medical implant 600, the proximal beam 670, and/or the core wire 30, the core wire 30 may be proximally retracted from the occlusive medical implant 600 and/or the proximal beam 670 to leave the occlusive medical implant 600 implanted within the left atrial appendage 50.

Figure 18:
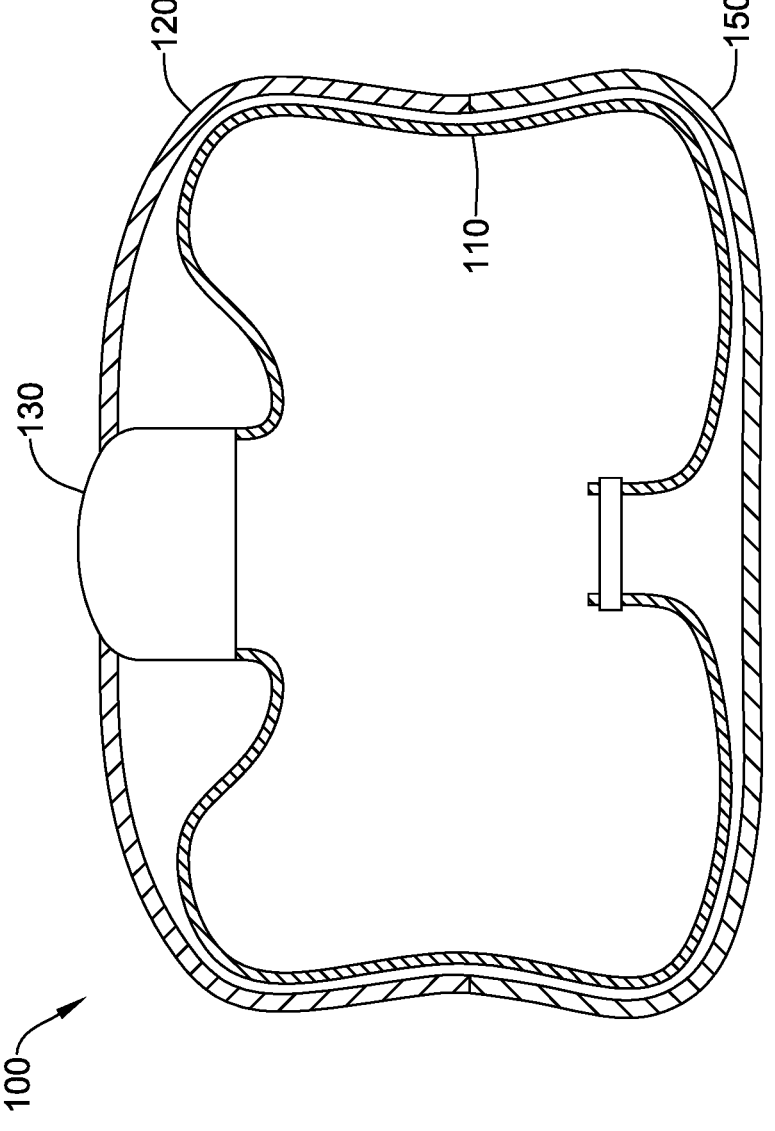
FIG. 18 is a partial cross-sectional view illustrating selected aspects of an implant for occluding a left atrial appendage.

In some alternative embodiments, the occlusive medical implant 100 (and/or any other occlusive medical implant described herein) may further include a second occlusive element 150 (e.g., a second membrane, a second fabric, or a second tissue element, etc.) connected to, disposed on, disposed over, disposed about, or covering a distal portion of the expandable framework 110 and/or the plurality of interconnected struts 112, as seen in FIG. 18. In some embodiments, the second occlusive element 150 may be connected to, disposed on, disposed over, disposed about, or cover a distal portion of an outer (or outwardly facing) surface of the expandable framework 110 and/or the plurality of interconnected struts 112. In some embodiments, the second occlusive element 150 may be connected to, disposed on, disposed over, disposed about, or covering the distal end of the expandable framework 110. Some, all, or none of the features described herein with respect to the occlusive element 120 may also apply and/or be used with the second occlusive element 150, including but not limited to means of attachment to the expandable framework 110 and/or the plurality of interconnected struts 112.

In some embodiments, the occlusive element 120 and the second occlusive element 150 may combine to substantially cover the expandable framework 110. In some embodiments, the occlusive element 120 and the second occlusive element 150 may combine to completely cover the expandable framework 110, except for the proximal hub 130. In some embodiments, the occlusive element 120 and the second occlusive element 150 may combine to completely cover the expandable framework 110, including the proximal hub 130. Other configurations are also contemplated.

In some embodiments, the second occlusive element 150 may be formed from the same material or a different material than the occlusive element 120. In some embodiments, a thickness of the second occlusive element 150 may be greater than a thickness of the occlusive element 120. In some embodiments, a surface roughness of the second occlusive element 150 may be greater than a surface roughness of the occlusive element 120. In some embodiments, a coefficient of friction between the second occlusive element 150 and the left atrial appendage 50 (e.g., when the occlusive medical implant 100 is disposed within the left atrial appendage 50) may be greater than a coefficient of friction between the occlusive element 120 and the left atrial appendage 50 (e.g., when the occlusive medical implant 100 is disposed within the left atrial appendage 50). In some embodiments, a porosity of the second occlusive element 150 may be greater than a porosity of the occlusive element 120. In some embodiments, the second occlusive element 150 may provide increased and/or improved fixation within the left atrial appendage 50 than using the occlusive element 120 alone.

The second occlusive element 150 may be optionally used on and/or with any occlusive medical implant 100 disclosed herein. Some suitable, but non-limiting, examples of materials for the second occlusive element 150, including but not limited to polymeric materials, fabrics, textiles, etc., are discussed below.

The materials that can be used for the various components of the system (and/or other elements disclosed herein) and the various components thereof disclosed herein may include those commonly associated with medical devices and/or systems. For simplicity purposes, the following discussion refers to the system. However, this is not intended to limit the devices and methods described herein, as the discussion may be applied to other elements, members, components, or devices disclosed herein, such as, but not limited to, the occlusive medical implant, the catheter, the core wire, the expandable framework, the occlusive element(s), etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS:

R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

In at least some embodiments, portions or all of the system and/or other elements disclosed herein may also be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids a user in determining the location and/or orientation of the system and/or other elements disclosed herein. Some examples of radiopaque materials can include, but are not limited to, gold, platinum, palladium, tantalum, tungsten alloy, polymer material loaded with a radiopaque filler, and the like.

In some embodiments, a degree of Magnetic Resonance Imaging (MM) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an Mill image. The system or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system and/or other elements disclosed herein may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane (for example, Polyurethane 85A), polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b- styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive medical implant for implantation within a left atrial appendage, comprising:
an expandable framework configured to self-expand from a collapsed configuration to an expanded configuration;
an occlusive element disposed on a proximal portion of the expandable framework;
a distal hub fixedly attached to a distal end of the expandable framework, the distal hub including a central aperture; and
a distal beam extending proximally from the distal hub within an interior of the expandable framework, the distal beam including a distal neck extending through the central aperture of the distal hub to a distal flange disposed distal of a distalmost surface of the distal hub, the distal flange having a radial extent greater than a diameter of the central aperture;
wherein the distal neck is configured to rotate within the central aperture without transferring rotation to the distal hub;
wherein at least a portion of the expandable framework is mechanically expandable from the expanded configuration to a securement configuration;
wherein when the occlusive medical implant is disposed within the left atrial appendage, the expandable framework exerts a first radial force on the left atrial appendage in the expanded configuration and the expandable framework exerts a second radial force on the left atrial appendage in the securement configuration;
wherein the second radial force is greater than the first radial force;
wherein rotation of the distal beam relative to the distal hub changes an axial position of the distal hub relative to the proximal hub.

2. The occlusive medical implant of claim 1, further comprising:
a proximal hub fixedly attached to a proximal end of the expandable framework; and
a proximal beam extending distally from the proximal hub within an interior of the expandable framework;
wherein the distal beam is engaged with the proximal beam.

3. The occlusive medical implant of claim 2, wherein the distal beam is axially movable relative to the proximal beam.

4. The occlusive medical implant of claim 2, wherein the proximal beam is fixedly attached to the proximal hub.

5. The occlusive medical implant of claim 4, wherein the distal beam is rotatable relative to the proximal beam.

6. The occlusive medical implant of claim 1, further including a second occlusive element disposed on a distal portion of the expandable framework, wherein:

a thickness of the second occlusive element is greater than a thickness of the occlusive element; or a surface roughness of the second occlusive element is greater than a surface roughness of the occlusive element; or a coefficient of friction between the second occlusive element and the left atrial appendage is greater than a coefficient of friction between the occlusive element and the left atrial appendage; or a porosity of the second occlusive element is greater than a porosity of the occlusive element.

7. A medical device system, comprising:

a catheter having a lumen extending from a proximal opening to a distal opening;

a core wire slidably disposed within the lumen; and an occlusive medical implant for implantation within a left atrial appendage releasably attached at a distal end of the core wire, the occlusive medical implant comprising:

an expandable framework configured to self-expand from a collapsed configuration to an expanded configuration when unconstrained by the catheter; and an occlusive element disposed over at least a portion of the expandable framework;

a distal hub fixedly attached to a distal end of the expandable framework, the distal hub including a central aperture; and a distal beam extending proximally from the distal hub within an interior of the expandable framework, the distal beam including a distal neck extending through the central aperture of the distal hub to a distal flange disposed distal of a distalmost surface of the distal hub, the distal flange having a radial extent greater than a diameter of the central aperture;

wherein the distal neck is configured to rotate within the central aperture without transferring rotation to the distal hub;

wherein at least a portion of the expandable framework is mechanically expandable from the expanded configuration to a securement configuration;

wherein when the occlusive medical implant is disposed within the left atrial appendage, the expandable framework exerts a first radial force on the left atrial appendage in the expanded configuration and the expandable framework exerts a second radial force on the left atrial appendage in the securement configuration;

wherein the second radial force is greater than the first radial force.

8. The medical device system of claim 7, wherein the core wire is rotatable relative to the occlusive medical implant.

9. The medical device system of claim 7, wherein the expandable framework is devoid of radially protruding anchor elements.

10. An occlusive medical implant for implantation within a left atrial appendage, comprising:

an expandable framework configured to self-expand from a collapsed configuration to an expanded configuration; and an occlusive element disposed on a proximal portion of the expandable framework;

a distal hub fixedly attached to a distal end of the expandable framework, the distal hub including a central aperture; and a distal beam extending proximally from the distal hub within an interior of the expandable framework, the distal beam including a distal neck extending through the central aperture of the distal hub to a distal flange disposed distal of a distalmost surface of the distal hub, the distal flange having a radial extent greater than a diameter of the central aperture;

wherein the distal neck is configured to rotate within the central aperture without transferring rotation to the distal hub;

wherein at least a portion of the expandable framework is mechanically expandable from the expanded configuration to a securement configuration;

wherein the expandable framework has a first radialmost outer extent in the expanded configuration and a second radialmost outer extent in the securement configuration;

wherein the second radialmost outer extent is greater than the first radialmost outer extent;

wherein rotation of the distal beam is configured to shift the expandable framework from the expanded configuration to the securement configuration.

* * * * *